(12) United States Patent
Hogrefe et al.

(10) Patent No.: US 6,803,216 B2
(45) Date of Patent: Oct. 12, 2004

(54) COMPOSITIONS AND METHODS FOR RANDOM NUCLEIC ACID MUTAGENESIS

(75) Inventors: Holly H. Hogrefe, San Diego, CA (US); Janice M. Cline, San Marcos, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 10/154,206

(22) Filed: May 23, 2002

(65) Prior Publication Data

US 2003/0152944 A1 Aug. 14, 2003

Related U.S. Application Data

(60) Provisional application No. 60/294,341, filed on May 30, 2001.

(51) Int. Cl.⁷ ................................. C12P 19/34
(52) U.S. Cl. ..................................... 435/91.2
(58) Field of Search ....................... 435/91.2; 536/24.1, 536/23.7

(56) References Cited

U.S. PATENT DOCUMENTS

| | | | | |
|---|---|---|---|---|
| 5,436,149 A | * | 7/1995 | Barnes | 435/194 |
| 5,489,523 A | | 2/1996 | Mathur | 435/194 |
| 5,545,552 A | | 8/1996 | Mathur | 435/252.3 |
| 5,556,772 A | | 9/1996 | Sorge et al. | 435/91.2 |
| 6,183,997 B1 | * | 2/2001 | Hogrefe | 435/91.2 |
| 6,350,580 B1 | | 2/2002 | Sorge | 435/6 |
| 2003/0049614 A1 | * | 3/2003 | Hogrefe et al. | 435/6 |

OTHER PUBLICATIONS

Leung et al "A Method for Random Mutagenesis of a Defined DNA Segment using a Modified Polymerase Chain Reaction" (1989), Technique (1:11–15.*
The Stratagene Catalog, p. 39 (1988).*
Cline, et al.; "PCR fidelity of Pfu DNA polymerase and other thermostable DNA polymerases"; (1996); *Nucleic Acids Res.*; 24: 3546–3551.
R. Craig Cadwell and Gerald F. Joyce; "Randomization of Genes by PCR Mutagenesis"; (1992); *PCR Methods Appl.*; 2: 28–33.
Leung, et al.; "A Method for Random Mutagenesis of a Defined DNA Segment Using a Modified Polymerase Chain Reaction"; (1989); *Technique*; 1: 11–15.
Shafikhani, et al.; "Generation of Large Libraries of Random Mutants in *Bacillus subtilis* by PCR–Based Plasmid Multimerization"; (1997); *BioTechniques*; 23: 304–310.
Alexandre Melnikov and Philip J. Youngman; "Random mutagenesis by recombinational capture of PCR products in *Bacillus subtilis* and *Acinetobacter calcoaceticus*"; (1999); *Nucleic Acids Res.*; 27: 1056–1062.
Yoshiaki Nishiya and Tadayuki Imanaka; "Alteration of Substrate Specificity and Optimum pH of Sarcosine Oxidase by Random and Site–Directed Mutagenesis"; (1994); *Appl. Env. Microbiol.*; 60: 4213–4215.
I. You and F.H. Arnold; "Directed evolution of subtilisin E in *Bacillus subtilis* to enhance total activity in aqueous dimethylformamide"; (1994); *Protein Eng.*; 9: 77–83.
William P.C. Stemmer; "DNA shuffling by random fragmentation and reassembly: In vitro recombination for molecular evolution"; (1994); *PNAS USA*; 91: 10747–10751.
Vartanian, et al.; "Hypermutagenic PCR involving all four transitions and a sizeable proportion of transversions"; (1996); *Nucleic Acids Res.*; 24: 2627–2631.

* cited by examiner

*Primary Examiner*—Kenneth R. Horlick
(74) *Attorney, Agent, or Firm*—Kathleen M. Williams; Palmer & Dodge, LLP

(57) ABSTRACT

The invention relates to compositions and methods for nucleic acid PCR mutagenesis using novel error-prone DNA polymerases and a PCR enhancing factor. The invention also relates to compositions and methods for nucleic mutagenesis with two or more DNA polymerases lacking or exhibiting reduced exonuclease activity. The invention further relates to kit format of said compositions for PCR mutagenesis.

31 Claims, 5 Drawing Sheets

COMPOSITIONS AND METHODS FOR RANDOM NUCLEIC ACID MUTAGENESIS

RELATED APPLICATIONS

This application claims the priority of U.S. Ser. No. 60/294,341, filed May 30, 2001, which is incorporated herein by reference in its totality, including tables and drawings.

TECHNICAL FIELD

The invention relates to random nucleic acid mutagenesis using exo– DNA polymerases.

BACKGROUND

PCR-based random mutagenesis is widely used for elucidating structure-function relationships of proteins, and for improving protein function (e.g., directed protein evolution) (Cadwell, R. C. and Joyce, G. F. 1992. Randomization of genes by PCR mutagenesis. PCR Methods Appl. 2:28–33; Leung, D. W., Chen, E., and Goeddel, D. V. 1989. A method for random mutagenesis of a defined DNA segment using a modified polymerase chain reaction. Technique 1:11–15). The procedure involves amplifying a gene or portion of a gene under mutagenic conditions, cloning the PCR fragments, and then screening the resulting library for novel mutations that affect protein activity (Melnikov, A. and Youngman, P. J. 1999. Random mutagenesis by recombinational capture of PCR products in *Bacillus subtilis* and *Acinetobacter calcoaceticus*. Nucleic Acids Res. 27:1056–1062; Wan, L., Twitchett, M. B., Eltis, L. D., Mauk. A. G., and Smith, M. 1998. In vitro evolution of horse heart myoglobin to increase peroxidase activity. Proc. Natl. Acad. Sci. U.S.A. 95:12825–12831; You, L. and Arnold, F. H. 1996. Directed evolution of subtilisin E in *Bacillus subtilis* to enhance total activity in aqueous dimethylformamide. Protein Eng. 9:77–83). Mutations are deliberately introduced during PCR through the use of error-prone DNA polymerases and reaction conditions. To analyze structure-function relationships, mutation rates of 1 mutation per gene are desired to assess the contribution of individual amino acids to protein function (Vartanian, J. P., Henry, M., and Wain-Hobson, S. 1996. Hypermutagenic PCR involving all four transitions and a sizeable proportion of transversions. Nucleic Acids Res. 24:2627–2631). For directed evolution, mutagenesis rates of 2 to 7 mutations per gene are considered the most effective for creating mutant libraries and isolating proteins with enhanced activities (Cherry, J. R. Lamsa, M. H., Schneider, P., Vind, J., Svendsen, A., Jones, A., and Pedersen, A.H. 1999. Directed evolution of a fungal peroxidase. Nat. Biotechnol. 17:379–384; Shafikhani, S., Siegel, R. A., Ferrari, E., and Schellenberger, V. 1997. Generation of large libraries of random mutants in *Bacillus subtilis* by PCR-based plasmid multimerization. BioTechniques 23:304–310; Wan, L., Twitchett, M. B., Eltis, L. D., Mauk. A. G., and Smith, M. 1998. In vitro evolution of horse heart myoglobin to increase peroxidase activity. Proc. Natl. Acad. Sci. U.S.A. 95:12825–12831; You, L. and Arnold, F. H. 1996. Directed evolution of subtilisin E in *Bacillus subtilis* to enhance total activity in aqueous dimethylformamide. Protein Eng. 9:77–83). Mutation rates greater than 7 mutations per gene typically result in loss of protein activity, although proteins with improved activities have been successfully isolated from highly mutagenized libraries exhibiting up to 20 mutations per gene (Daugherty, P. S., Chen, G., Iverson, B. L., and Georgiou, G. 2000. Quantitative analysis of the effect of the mutation frequency on the affinity maturation of single chain Fv antibodies. Proc. Natl. Acad. Sci. U.S.A. 97:2029–2034).

Conventional methods employ Taq DNA polymerase, as it lacks proofreading activity and is inherently error prone. To achieve useful mutation frequencies, the error rate of Taq (1 mutation per ~125,000 bases (Cline, J., Braman, J. C. and Hogrefe, H. H. 1996. PCR fidelity of Pfu DNA polymerase and other thermostable DNA polymerases. Nucleic Acids Res. 24:3546–3551) is further increased by employing PCR reaction buffers that contain $Mn^{2+}$ and/or unbalanced nucleotide concentrations (Cadwell, R. C. and Joyce, G. F. 1992. Randomization of genes by PCR mutagenesis. PCR Methods Appl. 2:28–33; Leung, D. W., Chen, E., and Goeddel, D. V. 1989. A method for random mutagenesis of a defined DNA segment using a modified polymerase chain reaction. Technique 1:11–15). In the presence of 7 mM $MgCl_2$, 0.5 mM $MnCl_2$, 1 mM dCTP and TTP, and 0.2 mM dGTP and dATP, Taq incorporates 4.9 to 6.6 mutations per kb per PCR (Cadwell, R. C. and Joyce, G. F. 1992. Randomization of genes by PCR mutagenesis. PCR Methods Appl. 2:28–33; Shafikhani, S., Siegel, R. A., Ferrari, E., and Schellenberger, V. 1997. Generation of large libraries of random mutants in *Bacillus subtilis* by PCR-based plasmid multimerization. BioTechniques 23:304–310). Under these conditions, mutational bias is regarded as minimal or skewed to favor mutations at AT base pairs. Lower mutation frequencies can be obtained by reducing $MnCl_2$ concentration (1–2 mutations per kb), while higher mutation frequencies (>6 mutations per kb) are achieved by performing consecutive PCRs or by selectively increasing dGTP concentration (Melnikov, A. and Youngman, P. J. 1999. Random mutagenesis by recombinational capture of PCR products in *Bacillus subtilis* and *Acinetobacter calcoaceticus*. Nucleic Acids Res. 27:1056–1062; Nishiya, Y. and Imanaka, T. 1994. Alteration of substrate specificity and optimum pH of sarcosine oxidase by random and site-directed mutagenesis. Appl. Env. Microbiol. 60:4213–4215; You, L. and Arnold, F. H. 1996. Directed evolution of subtilisin E in *Bacillus subtilis* to enhance total activity in aqueous dimethylformamide. Protein Eng. 9:77–83).

Although widely used, Taq-based methods exhibit significant drawbacks that limit the utility of PCR random mutagenesis methods. First, amplification under mutagenic conditions ($Mn^{2+}$, unbalanced nucleotide pools) reduces the activity of Taq and limits random mutagenesis to DNA sequences less than 1-kb in length (Leung, D. W., Chen, E., and Goeddel, D. V. 1989. A method for random mutagenesis of a defined DNA segment using a modified polymerase chain reaction. Technique 1:11–15; Stemmer, W. P. 1994. DNA shuffling by random fragmentation and reassembly: in vitro recombination for molecular evolution. Proc. Natl. Acad. Sci. USA 91:10747–10751). Second, PCR products are amplified in lower yield using mutagenic reaction conditions (Vartanian, J. P., Henry, M., and Wain-Hobson, S. 1996. Hypermutagenic PCR involving all four transitions and a sizeable proportion of transversions. Nucleic Acids Res. 24:2627–2631), which can reduce cloning efficiency and library size. Third, preparing and using multiple buffers (varying $MnCl_2$ and dNTP concentrations) to construct a series of libraries with different mutation frequencies is time-consuming and can produce variable results. Finally, altering nucleotide ratios to achieve high mutation frequencies (>6 mutations per kb) can lead to strong bias in the types of mutations produced. For example, selectively increasing dGTP concentration favors AT→GC transitions, which accounted for 70% of all mutations in one study (You, L. and Arnold, F. H. 1996. Directed evolution of subtilisin E in

*Bacillus subtilis* to enhance total activity in aqueous dimethylformamide. Protein Eng. 9:77–83).

There is a need in the art for random mutagenesis of nucleic acid longer than 1 kb. There is also a need to improve the yield of the final mutated product to facilitate subsequent cloning of the product. There is further a need for a novel error prone DNA polymerase which minimizes mutation bias or produces a different mutational bias than a given polymerase produces. Finally, there is a need for a simplified PCR mutagenesis conditions to achieve various mutation frequencies.

SUMMARY OF THE INVENTION

The invention is related to novel compositions and methods for nucleic acid mutagenesis.

The invention provides a composition for PCR mutagenesis comprising an archaeal exo– DNA polymerase which substantially lacks 3' to 5' exonuclease activity, and PCR enhancing factor.

In a preferred embodiment, the archaeal exo– DNA polymerase is selected from the group consisting of: exo–Tli DNA polymerase, exo– Pfu DNA polymerase, exo– KOD DNA polymerase, exo– JDF-3 DNA polymerase, and exo–PGB-D DNA polymerase.

The invention also provides a composition comprising an archaeal exo– DNA polymerase, PCR enhancing factor, and one or more DNA polymerases selected from the group consisting of Taq DNA polymerase, Tth DNA polymerase, UlTma DNA polymerase, exo–Tli DNA polymerase, exo– Pfu DNA polymerase, exo– Tma DNA polymerase, exo– KOD DNA polymerase, exo– JDF-3 DNA polymerase, and exo–PGB-D DNA polymerase, wherein said one or more DNA polymerases are different from said archaeal DNA polymerase.

Preferably the compositions mentioned above herein further comprise a PCR buffer useful for generating a mutated amplified product at a given mutation frequency.

More preferably, the PCR buffer lacks $Mn^{2+}$.

The compositions mentioned above-herein may further comprise equivalent molar amounts of dATP, dTTP, dGTP, and dCTP.

The invention provides a kit for PCR mutagenesis comprising an archaeal exo– DNA polymerase, PCR enhancing factor, and packaging means therefore.

The invention further provides the above-mentioned kit, further comprising one or more polymerases selected from a group consisting of Taq DNA polymerase, Tth DNA polymerase, UlTma DNA polymerase, exo–Tli DNA polymerase, exo– Pfu DNA polymerase, exo–Tli DNA polymerase, exo– Tma DNA polymerase, exo– KOD DNA polymerase, exo– JDF-3 DNA polymerase, and exo–PGB-D DNA polymerase, wherein said one or more DNA polymerases are different from said archaeal DNA polymerase.

The kits mentioned above-herein may further comprise a PCR buffer useful for generating a mutated amplified product at a given mutation frequency.

Preferably, the PCR buffer in the above mentioned kits lacks $Mn^{2+}$.

More preferably, the kits further comprise equivalent molar amounts of dATP, dTTP, dGTP, and dCTP.

The invention provides a method of PCR amplification for mutagenesis comprising incubating a reaction mixture comprising a nucleic acid template, at least two PCR primers, an archaeal exo– DNA polymerase, and PCR enhancing factor under conditions which permit amplification of said nucleic acid template by said archaeal exo– DNA polymerase to produce a mutated amplified product.

Preferably, the archaeal exo– DNA polymerase is selected from the group consisting of: Taq DNA polymerase, Tth DNA polymerase, UlTma DNA polymerase, exo–Tli DNA polymerase, exo– Pfu DNA polymerase, exo– Tma DNA polymerase, exo– KOD DNA polymerase, exo– JDF-3 DNA polymerase, and exo–PGB-D DNA polymerase.

The above-mentioned method, may further comprise incubating one or more exo– DNA polymerases selected from a group consisting of: Taq DNA polymerase, Tth DNA polymerase, UlTma DNA polymerase, exo–Tli DNA polymerase, exo– Pfu DNA polymerase, exo–Tli DNA polymerase, exo– Tma DNA polymerase, exo– KOD DNA polymerase, exo– JDF-3 DNA polymerase, and exo–PGB-D DNA polymerase in said reaction mixture, wherein said one or more DNA polymerases are different from said archaeal DNA polymerase.

Preferably, said incubating step is performed in a PCR reaction buffer lacking $Mn^{2+}$.

Also preferably, said incubating step may further comprise incubating equivalent molar amounts of dATP, dTTP, dGTP, and dCTP.

Still preferably, said incubating step may generate said mutated amplified product at a given mutation frequency using a given amount of said nucleic acid template.

The method useful to the invention may comprise a first said incubating step which generates a first said mutated amplified product at a first given frequency using a first selected amount of said nucleic acid template, and a second said incubating step which generates a second said mutated amplified product at a second given frequency using a second selected amount of said nucleic acid template, wherein said first incubating step and second incubating step comprise a single buffer composition.

The method of the invention may further comprise subsequently repeating one or more additional said incubating step using a portion of or the total amplified product of a preceding incubating as template for a subsequent incubating step.

Preferably, the mutation frequency generated by the incubating step is proportional to the amount of said nucleic acid template.

The incubating step of the subject invention may comprise 1 pg to 1 µg of said nucleic acid template, which may produce said mutated amplified product from said nucleic acid template at a mutation frequency of 1,000 to 16,000 mutations or more per $10^6$ base pair.

The incubating step of the subject invention may comprise 10–100 ng of said nucleic acid template, which may produce said mutated amplified product at a mutation frequency of 1,000 to 3,000 mutations per $10^6$ base pair.

The incubating step of the subject invention may comprise 10 pg to 10 ng of said nucleic acid template, which may produce said mutated amplified product at a mutation frequency of 3,000 to 7,000 mutations per $10^6$ base pair.

The incubating step of the subject invention may comprise 10 pg to 10 ng of said nucleic acid template, which may produce said mutated amplified product at a mutation frequency of 7,000 to 16,000 or more mutations per $10^6$ base pair.

According to the instant invention, one or more additional said incubating steps may be repeated subsequently using a portion of or the total amplified product of a preceding incubating as template for a subsequent incubating to generate a mutation frequency of 7,000 to 16,000 or more mutations per $10^6$ base pair.

The nucleic acid template of the instant invention may be 0.1 kb to 10 kb in length.

The method of the instant invention may produce an amplified product at a yield of 0.5–10 μg.

DETAILED DESCRIPTION OF THE INVENTION

I. Definitions

Figure 1:
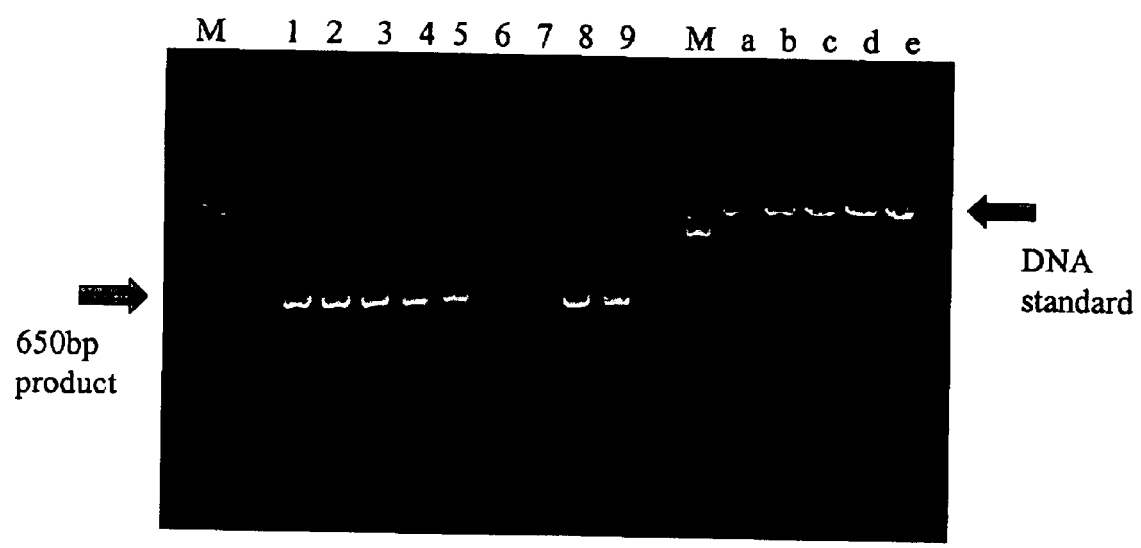
FIG. 1 illustrates the relationship between error-prone PCR yield and various amount of input DNA. Ethidium Bromide stained 1% agarose gel shows amplification of LacZ plasmid with Mutazyme. Amount of plasmid used is as follows: 1) 100 ng, 2) 10 ng, 3) 1 ng, 4) 100 pg, 5) 10 pg, 6) 1 pg, 7) 100 fg, 8) 1 ul of PCR #5 diluted 1:1000, 9) 1 ul of PCR #8 diluted 1:1000. Amount of DNA standard: a) 100 ng, b) 200 ng, c) 500 ng, d) 1 ug, e) 2 ug. Marker (M) is Stratagene's Kb ladder.

As used herein, "exonuclease" refers to an enzyme that cleaves bonds, preferably phosphodiester bonds, between nucleotides one at a time from the end of a nucleic acid. An exonuclease can be specific for the 5' or 3' end of a DNA or RNA molecule, and is referred to herein as a 5' to 3' exonuclease or a 3' to 5' exonuclease. An exonuclease according to the invention is a 3' to 5' exonuclease which degrades nucleic acid by cleaving successive nucleotides from the 3' end of the nucleic acid. During the synthesis or amplification of a nucleic acid template, a DNA polymerase with 3' to 5' exonuclease activity (exo+) has the capacity of removing mispaired base (proofreading activity), therefore is less error-prone than a DNA polymerase without 3' to 5' exonuclease activity (exo–). Wild type Tth DNA polymerase and Taq DNA polymerase are exo– because thay do not have 3' to 5' exonuclease activities, however, wild type Pfu DNA polymerase, E. coli DNA polymerase I, T7 DNA polymerase, Tma DNA polymerase, Tli DNA polymerase, KOD DNA polymerase, JDF DNA polymerse, and PGB-D DNA polymerase are exo+ because they all have 3' to 5' exonuclease activity. The exonuclease activity can be defined by methods well known in the art. For example, one unit of exonuclease activity may refer to the amount of enzyme required to cleave 1 μg DNA target in an hour at 37° C.

As used herein, "nucleic acid polymerase" refers to an enzyme that catalyzes the polymerization of nucleotides. Generally, the enzyme will initiate synthesis at the 3'-end of the primer annealed to a nucleic acid template sequence, and will proceed toward the 5' end of the template strand. "DNA polymerase" catalyzes the polymerization of deoxynucleotides. Known DNA polymerases include, for example, *Pyrococcus furiosus* (Pfu) DNA polymerase (Lundberg et al., 1991, *Gene*, 108:1), *E. coli* DNA polymerase I (Lecomte and Doubleday, 1983, *Nucleic Acids Res.* 11:7505), T7 DNA polymerase (Nordstrom et al., 1981, *J. Biol. Chem.* 256:3112), *Thermus thermophilus* (Tth) DNA polymerase (Myers and Gelfand 1991, *Biochemistry* 30:7661), *Bacillus stearothermophilus* DNA polymerase (Stenesh and McGowan, 1977, *Biochim Biophys Acta* 475:32), *Thermococcus litoralis* (Tli) DNA polymerase (also referred to as Vent DNA polymerase, Cariello et al., 1991, *Nucleic Acids Res*, 19:4193), 9° Nm DNA polymerase (discontinued product from New England Biolabs), *Thermotoga maritima* (Tma) DNA polymerase (Diaz and Sabino, 1998 *Braz J. Med. Res*, 31:1239), *Thermus aquaticus* (Taq) DNA polymerase (Chien et al., 1976, J. Bacteoriol, 127:1550), *Pyrococcus kodakaraensis* KOD DNA polymerase (Takagi et al., 1997, *Appl. Environ. Microbiol.* 63:4504), JDF-3 DNA polymerase (Patent application WO 0132887), and Pyrococcus GB-D (PGB-D) DNA polymerase (Juncosa-Ginesta et al., 1994, *Biotechniques*, 16:820). The polymerase activity of any of the above enzyme can be determined by means well known in the art. One unit of DNA polymerase activity, according to the subject invention, is defined as the amount of enzyme which catalyzes the incorporation of 10 mmoles of total dNTPs into polymeric form in 30 minutes at optimal temperature (e.g., 72° C. for Pfu DNA polymerase).

As used herein, "archaeal" refers to an organism or to a DNA polymerase from an organism of the kingdom Archaea.

As used herein, "substantially lacks 3' to 5' exonuclease activity" or "exonuclease deficient" refers to a DNA polymerase which exhibits 3' to 5' exonuclease activity of less than 100 units (U) per milligram (mg) of purified polymerase, preferably less than 50 U/mg, and more preferably less than 10 U/mg. Such an enzyme, according to the invention, is referred to as an "exo–" enzyme. An "exo–" enzyme may be made with abolished or reduced exonuclease activity through deletions or point mutations of the polynucleotide sequence encoding the exonuclease domain.

"exo–" DNA polymerases that are useful according to the invention include exo– Pfu DNA polymerase (a mutant form of Pfu DNA polymerase that substantially lacks 3' to 5' exonuclease activity, Cline et al., 1996, *Nucleic Acids Research*, 24:3546; U.S. Pat. No. 5,556,772; commercially available from Stratagene, La Jolla, Calif. Catalogue

600163), exo− Tma DNA polymerase (a mutant form of Tma DNA polymerase that substantially lacks 3' to 5' exonuclease activity), exo− Tli DNA polymerase (a mutant form of Tli DNA polymerase that substantially lacks 3' to 5' exonuclease activity; New England Biolabs, (Cat #257)), exo− E. coli DNA polymerase (a mutant form of E. coli DNA polymerase that substantially lacks 3' to 5' exonuclease activity) exo−klenow fragment of E.col; DNA polymerase I (Stratagene, Cat #600069), exo− T7 DNA polymerase (a mutant form of T7 DNA polymerase that substantially lacks 3' to 5' exonuclease activity), exo− KOD DNA polymerase (a mutant form of KOD DNA polymerase that substantially lacks 3' to 5' exonuclease activity), exo− JDF-3 DNA polymerase (a mutant form of JDF-3 DNA polymerase that substantially lacks 3' to 5' exonuclease activity), exo− PGB-D DNA polymerase (a mutant form of PGB-D DNA polymerase that substantially lacks 3' to 5' exonuclease activity) New England Biolabs, Cat. #259, Tth DNA polymerase, Taq DNA polymerase (e.g., Cat. Nos 600131, 600132, 600139, Stratagene La Jolla, Calif.); UlTma (N-truncated) *Thermatoga martima* DNA polymerase; Klenow fragment of DNA polymerase 1,9Nm DNA polymerase (discontinued product from New England Biolabs, Beverly, Mass.), and "3'−5' exo reduced" mutant (Southworth et al., 1996, Proc. Natl. Acad. Sci 93:5281).

As used herein, useful Taq DNA polymerase includes wild type Taq DNA polymerase and mutant forms of Taq DNA polymerase with reduced fidelity (e.g., Patel et al., 2001, J. Biol.Chem. 276:5044, hereby incorporated by reference).

As used herein, a "PCR enhancing Turbo factor (Turbo factor)" or a "Polymerase Enhancing Factor" (PEF) refers to a complex or protein possessing nucleic acid polymerase enhancing activity (Hogrefe, H., Scott, B., Nielson, K., Hedden, V., Hansen, C., Cline, J., Bai, F., Amberg, J., Allen, R., Madden, M.(1997) Novel PCR enhancing factor improves performance of Pfu DNA polymerase. *Strategies* 10(3):93–96; and U.S. Pat. No. 6,183,997, both of which are hereby incorporated as references). PEF, useful in the present invention, comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is determined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 mmole of PPi formed per hour (at 85° C.).

In some embodiments, 1 ng PEF preparation has an activity of 3–4 mmoles PPi/hour, which is 1 unit.

As used herein, the term "Mutazyme" refers to a composition comprising a mixture of exo− Pfu DNA polymerase and PEF. The composition may also include a storage buffer containing 50 mM Tris-HCl, pH 8.2; 0.1 mM EDTA, pH 8.2; 1 mM DTT; 0.1% (v/v) Igepal CA-630; 0.1% (v/v) Tween 20; and 50% Glycerol. exo− Pfu DNA polymerase and PEF can be mixed at different ratios as measured by their respective activities. For example, exo− Pfu DNA polymerase and PEF can be mixed at an activity ratio of from 40/1, 20/1, 15/1, 10/1, 5/1, 2/1, 1/1, 1/2, 1/5, 1/10, 1/20, 1/40, 1/100, 1/200, 1/300, 1/400, or lower. Preferably, the ratio of exo− Pfu DNA polymerase and PEF is between 2.5/1 to 40/1. The activity of Mutazyme, according to the invention, refers to the activity of exo− DNA polymerase, not the activity of PEF. Mutazyme may be stored at −20° C. till use.

As used herein, "mutation" refers to an alteration in a nucleic acid sequence. A mutation according to the invention can involve the removal, addition or substitution of a single nucleotide base within a DNA sequence, or they may be the consequence of changes involving the insertion or deletion of large numbers of nucleotides. A nucleic acid in which a mutation has occurred is called a "mutant". The term "mutagenesis" according to the invention refers to the introduction of mutations into a nucleic acid sequence.

As used herein, "mutation frequency" refers to the number of mutations per unit of base pair or unit of time, for example, the number of mutations per $10^6$ base pair or per PCR reaction. "Mutation frequency" also refers to the number of mutations per nucleotide sequence. In one embodiment, a low mutation frequency of 1–3000 (e.g., 1000–3000) per $10^6$ base pair is obtained. In another embodiment, a mutation frequency of 3000–7000 per $10^6$ base pair is obtained. In yet another embodiment, a mutation frequency of 7000–16000 per $10^6$ base pair is obtained by comprising one or more additional PCR amplification reactions.

Mutation frequency (M.F.), according to the invention, is related to the number of target duplications or the "d value". "d value" is calculated by the following relation: d log (A/B)/log2, wherein A is the yield of amplified mutated product, B is the starting amount of nucleic acid template. The amount of start template is not measured as the total amount of DNA in the reaction, but the amount of target DNA in the reaction, that is, the actual sequence to be mutagenized which resides between the two primer complementary sites. For example, if a 1 kb fragment is to be amplified from a 10 kb DNA template, the target amount (ng) is only 10% of the plasmid amount (ng) added to the PCR reaction. Alternatively, the amount of nucleic acid can be in molar quantities for the calculation of d value. The mutation frequency (M.F.) may be calculated according to M.F. =(error rate)×(number of base pairs)×(d). Because M.F. is related to d value, the mutation frequency can be controlled by controlling the "d value" or the number of times a target is duplicated in a PCR reaction.

As used herein, "amplification" refers to any in vitro method for increasing the number of copies of a nucleic acid template sequence with the use of a polymerase. Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR; Mullis and Faloona, 1987, *Methods Enzymol.*, 155:335). One PCR reaction may consist of 5 to 100 "cycles" of denaturation and synthesis of a nucleic acid molecule. PCR amplifications with an exo– DNA polymerase inherently will result in generating mutated amplified product.

As used herein, "polymerase chain reaction" or "PCR" refers to an in vitro method for amplifying a specific nucleic acid template sequence. The PCR reaction involves a repetitive series of temperature cycles and is typically performed in a volume of 50–100 $\mu$l. The reaction mix comprises dNTPs (each of the four deoxynucleotides dATP, dCTP, dGTP, and dTTP), primers, buffers, DNA polymerase, and nucleic acid template. The PCR reaction comprises providing a set of oligonucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of oligonucleotide primers" or "a set of PCR primers" can comprise two, three, four or more primers. In one embodiment, an exo– Pfu DNA polymerase is used to amplify a nucleic acid template in a PCR reaction.

As used herein, the term "PCR primer" refers to a single stranded DNA or RNA molecule that can hybridize to a nucleic acid template and prime enzymatic synthesis of a second nucleic acid strand. A PCR primer useful according to the invention is between 10 to 100 nucleotides in length, preferably 17–50 nucleotides in length and more preferably 17–45 nucleotides in length.

As used herein, a "PCR buffer lacking $Mn^{2+}$" refers to a PCR buffer which is prepared without the addition of an organic or inorganic $Mn^{2+}$ salt, although the buffer may contain a small amount of endogenous $Mn^{2+}$. A buffer lacking $Mn^{2+}$ contains less than 100 $\mu$M $Mn^{2+}$, for example, less than 50 $\mu$M $Mn^{2+}$ or less than 10 $\mu$M $Mn^{2+}$.

As used herein, a "universal PCR reaction buffer" or "universal reaction buffer" refers to a single buffer composition which allows PCR amplification of a nucleic acid template by Mutazyme. The buffer may contain any known chemicals used in a buffer for PCR reaction. Preferably, the buffer contains a buffering composition selected from Tris or Tricine. More preferably, the buffering composition has a pH range of from 7.5 to 9.5. Preferably, the universal PCR reaction buffer contains $Mg^{2+}$ (e.g., $MgCl_2$ or $MgSO_4$) in the range of 1–10 mM. The buffer according to the invention may also contain K+ (e.g., KCl) in the range of from 0 to 20 mM. In some embodiments, the buffer contains components which enhances PCR yield (e.g., $(NH_4)_2SO_4$ in the range of from 0 to 20 mM). In other embodiments, the buffer contains one or more non-ionic detergents (e.g., Trition X-100, Tween 20, or NP40, in the range of from 0 to 1%). The buffer may also contain BSA in the range of from 1–100 $\mu$g/ml. In a preferred embodiment of the invention, the universal PCR reaction buffer contains 10 mM KCl, 10 mM $(NH_4)_2SO_4$, 20 mM Tris-Cl (pH 8.8), 2 mM $MgSO_4$, 0.1% Triton X-100, 100 $\mu$g/ml BSA. In another preferred embodiment, the buffer contains 10 mM KCl, 10 mM $(NH_4)_2SO_4$, 20 mM Tris-Cl (pH 9.2), 2 mM $MgSO_4$, 0.1% Triton X-100, 100 $\mu$g/ml BSA.

As used herein, the term "equivalent amount(s)" refers to components (e.g., dATP, dTTP, dGTP, and dCTP) in the PCR buffer having an equal molar concentration.

As used herein, the term "unbalanced dNTP concentration" refers to an unequal molar concentration of dATP, dTTP, dGTP, and dCTP in the PCR reaction mixture. For example, an "unbalanced dNTP concentration" may have more dCTP and dTTP than dATP and dGTP.

As used herein, an "amplified product" refers to the double strand nucleic acid population at the end of a PCR amplification reaction. The amplified product contains the original nucleic acid template and nucleic acid synthesized by DNA polymerase using the nucleic acid template during the PCR reaction. The amplified product, according to the invention, contains mutations to the original nucleic acid template sequence due to the use of error-prone DNA polymerases in the PCR reaction, e.g., Mutazyme and Taq DNA polymerases.

As used herein, a "mutant nucleic acid library" or a "mutant library" refers to a nucleic acid library comprising a collection of mutant nucleic acids representing a number of different mutations as defined herein, derived from one or more nucleic aid templates. The "complexity of a mutant nucleic acid library" refers to the number of different mutations represented in the library. Preferably a mutant nucleic acid library, according to the invention, is prepared by PCR mutagenesis using exo– Pfu DNA polymerase. In one embodiment, a mutant nucleic acid library is prepared by exo– Pfu DNA polymerase and another exo– DNA polymerase selected from the group consisting of: Taq DNA polymerase, exo– *E. coli* DNA polymerase, exo–Tli DNA polymerase, exo– Tma DNA polymerase, exo–Tth DNA polymerase, exo–KOD DNA polymerase, 9° Nm DNA polymerase, exo–Tma DNA polymerase and exo– PGB-D DNA polymerase. In another preferred embodiment, a mutant nucleic acid library is prepared by PCR mutagenesis using exo– Pfu DNA polymerase and Taq DNA polymerase. In another embodiment, a mutant library is generated by repeating one or more additional PCR amplification reactions.

As used herein, the term "repeating one or more additional subsequent PCR amplification reactions" refers to the subsequent performance of one or more additional PCR amplification reactions comprising incubating a nucleic acid template, at least two PCR primers, an error-prone DNA polymerase under conditions which permit amplification of the nucleic acid template. A subsequent PCR reaction comprises said incubating step using the PCR amplified product of a preceding PCR amplification as template. The amplified product of a preceding PCR amplification reaction may be purified before being used as template for a subsequent PCR reaction by means known in the art, e.g., phenol extraction/ ethanol precipitation or column purification. The template for a subsequent PCR amplification reaction may be a portion of or the total amplified product of a preceding PCR amplification. For each subsequent PCR amplification, fresh reagents (e.g., reaction buffer, dNTP, DNA polymerase, primers) are added to the reaction mixture. If a portion of the amplified product of a preceding PCR amplification is used, the volume of a subsequent PCR reaction may be the same as the preceding PCR reaction. If the total amplified product of a preceding PCR reaction is used as template, a subsequent PCR reaction will have larger volume than the preceding PCR reaction.

As used herein, a "mutation spectrum" refers to the presence in mutated amplified PCR product of different mutation frequencies of different types of mutations generated from a nucleic acid template by PCR mutagenesis using one or more given DNA polymerases. Each DNA polymerase may have its unique mutation spectrum due to its unique bias in generating mutations (Andre, P., Kim, A., Khrapko, K. and Thilly, W. G. (1997) Fidelity and mutational spectrum of Pfu DNA polymerase on a human mitochondrial DNA sequence. *Genome Res.* 7:843–852; Keohavong, P., Ling, L., Dias, C. and Thilly, W. G. (1993) Predominant mutations induced by the *Thermococcus litoralis*, Vent polymerase during DNA amplification in vitro. *PCR Methods Applic.* 2:288–292; Shafikhani, et al., 1997, Generation of large libraries of random mutants in *Bacillus subtilis* by PCR-based plasmid multimerization, Biotechniques 23 :304–310). Different types of mutations which occur in a DNA molecule are described as transition (Ts), transversion (Tv), GC, or AT mutations. Bias in mutation spectrum can be assessed by calculating the Ts/Tv and GC/AT ratios. As used herein, a "GC/AT ratio" refers to a ratio between GC mutation frequency wherein nucleotide G or C of a nucleic acid template is mutated to nucleotide A or T and AT mutation frequency wherein nucleotide A or T of a nucleic acid template is mutated to nucleotide G or C in a PCR reaction. As used herein, "transition" refers to a single base pair mutation wherein a pyrimidine (T or C) is substituted by another pyrimidine (C or T respectively) or a purine (A or G) is substituted by another purine (G or A respectively). As used herein, "transversion" refers to a single base pair mutation wherein a purine (A or G) is replaced by a pyrimidine (C or T) or a pyrimidine (C or T) is replaced by a purine (A or G). There are four possible transitions: A→G, T→C, G→A, and C→T. There are eight possible transversions: A→T, T→A, A→C, C→A, T→G, G→T, G→C, and C→G. If a DNA polymerase lacks bias, the GC/AT ratio of the mutation spectrum generated by the DNA polymerase would be 1 and the Ts/Tv ratio of the mutation spectrum generated by the DNA polymerase would be 0.5.

As used herein, "proportional" refers to a numeric relationship between mutation frequency and the amount of nucleic acid template, wherein the mutation frequency increases as the amount of nucleic acid template in the PCR reaction decreases. In one embodiment, a "low" mutation frequency of 1000–3000 mutations per $10^6$ base pair is obtained employing 10–100 ng DNA template. In another embodiment, a "medium" mutation frequency of 3000–7000 mutations per $10^6$ base pair is obtained employing 10 pg-10 ng DNA template. In yet another embodiment, a "high" mutation frequency of 7000–16000 mutations per $10^6$ base pair, or a frequency greater than 16,000 mutations per $10^6$ base pair, is obtained by repeating one or more additional PCR amplification reactions.

As used herein, "nucleic acid template" or "target nucleic acid template" refers to a nucleic acid containing an amplified region. The "amplified region," as used herein, is a region of a nucleic acid that is to be either synthesized or amplified by polymerase chain reaction (PCR). For example, an amplified region of a nucleic acid template resides between two sequences to which two PCR primers are complementary to.

II. exo− Pfu DNA Polymerase

The wild type Pfu DNA plymerase can be purified from hyperthermophilic, marine archaebacterium, *Pyrococcus furiosus* (Pfu) as described (U.S. Pat. No. 5,545,552; Cline et al., 1996, Nucleic acid Research, 24:3546–3551). The wild type enzyme has an inherent 3' to 5' exonuclease activity which proofreads the synthesized DNA strand and allows a low error rate of $1.3 \times 10^{-6}$ nutation frequency per base pair per duplication during nucleic acid synthesis and amplification. The enzyme is extremely thermostable through a temperature range of about 0° C. to about 104° C., and exhibits DNA polymerase activity in temperatures of from about 40° C. to 90° C., with an activity optimum at about 72–75° C., which is limited by melting of DNA templates.

exo− Pfu DNA polymerase substantially lacks the 3' to 5' exonuclease activity, and therefore is error prone. exo–Pfu DNA polymerase exhibits an error prone rate of $4.7 \times 10^{-5}$ which is about 6 fold higher than the error rate of Taq DNA polymerase (Cline, J., Braman, J. C. and Hogrefe, H. H. (1996) PCR fidelity of Pfu DNA polymerase and other thermostable DNA polymerases. *Nucleic Acids Res.* 24(18) :3546–3551).

The exo− Pfu DNA polymerase can be prepared by any recombinant DNA techniques from the wild type Pfu DNA polymerase as described in U.S. Pat. No. 5,489,523, incorporated herein as reference. Other recombinant DNA techniques are also known in the art (For example, Ausubel et al., John Weley & Sons, Inc., 1997, *Current Protocols in Molecular Biology*).

Preferably, the exo− Pfu DNA polymerase has an amino acid residue sequence that substantially corresponds to the amino acid residue sequence of the wild type Pfu enzyme, except for certain specified substitutions to produce the desired deficiency in exonuclease. By "substantially corresponds" means that the sequence is at least 80% homologous, preferably at least 90% homologous, and more preferably is at least 98% homologous to the wild type enzyme.

The exo− Pfu DNA polymerase may be made by selective substitution of nucleotides encoding amino acid residues required for the 3' to 5' exonuclease activity of the wild type Pfu enzyme without inhibiting the DNA polymerase activity. An exo− Pfu DNA polymerase preferably has a DNA polymerase activity, expressed as specific activity, of at least about 10,000 units (10 KU) per mg of polymerase protein, and preferably at least about 15 KU/mg, and more preferably at least 25 KU/mg. One unit of polymerase activity is defined as the amount of enzyme which catalyzes the incorporation of 10 mmoles of total dNTP into polymeric form in 30 minutes at optimal temperature for each enzyme (e.g., 72° C. for Pfu DNA polymerase). Polymerase concentrations (U/µl) are extrapolated from the slope of the linear portion of units vs. enzyme volume plots, this format for indicating enzyme amount is well known in the art.

The apparent molecular weight of the wild type Pfu DNA polymerase protein is about 90,000–93,000 daltons as determined by SDS-PAGE under denaturing conditions. Preferred exo− Pfu DNA polymerase proteins have the same apparent molecular weight as the wild type polymerase.

Preferably, Exo− Pfu DNA polymerase retains the thermostability of the wild type Pfu DNA polymerase and functions effectively in PCR reaction. Stated differently, the exo− Pfu enzyme does not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. More preferably, the enzyme preferably does not become irreversibly denatured at about 90–100° C. That is, the enzyme loses less than 25 percent of its DNA polymerase activity after exposure to 95° C. for 1 hour (hr), more preferably less than 10%, and yet more preferably less than 5% of its activity.

One form of the exo– Pfu DNA polymerase is commercially available from Stratagene (Catalogue #600163, La Jolla, Calif.). However, the subject invention is also intended to include other forms of exo– Pfu DNA polymerases made by any recombinant DNA techniques, for example, techniques disclosed in U.S. Pat. No. 5,489,523, which can be relied on by one skilled in the art in making and using exo– Pfu DNA polymerase. The referred reference (U.S. Pat. No. 5,489,523), therefore, is specifically incorporated, in its entirety, into this disclosure. The other forms of exo– Pfu DNA polymerases include N-terminal or C-terminal truncation, and point mutations in 3'-5' exonuclease domain and ancillary domains (e.g., partitioning domains).

III. PCR Enhancing Factor PEF

Proteins with PCR enhancing activity can be produced from a bacterial or an archeabacterial source. PEFs can be polymerase enhancing activity mixtures of one or more such proteins, protein complexes containing one or more such proteins, or extracts containing one or more of such proteins, mixtures or complexes. The Pfu P45 and P50 proteins are illustrative of PEF proteins P45 and P50, which exhibit an apparent molecular weight of approximately 45 kD and 50 kD. These two proteins are predominant components of a PEF complex derivable from *Pyrococcus furiosus* (Pfu) as described by U.S. Pat. No. 6,183,997. The P45 protein appears to be the most active component, although full activity or stability may also require the presence of the P50 component. Preferably, homogenous PEF made by recombinant DNA techniques from a bacterial host other than Pfu is used in the subject invention to avoid any contamination of wild type Pfu DNA polymerase which may result in the reduction of mutation frequency of exo– Pfu DNA polymerase. However, the present invention is intended to encompass other PEF proteins, mixtures, complexes, and extracts derived from organisms other than Pfu, or by use of the structural information on the PEF proteins described as in U.S. Pat. No. 6,183,997. The referred reference (U.S. Pat. No. 6,183,997), therefore, is specifically incorporated, in its entirety, into this disclosure.

IV. Mutazyme

Mutazyme is prepared by mixing exo–Pfu DNA polymerase with PCR enhancing factor PEF. The ratio of the amount of the exo– Pfu DNA polymerase (as indicated by its polymerase activity unit) and the amount of the PEF (as indicated by its PCR enhancing activity unit) in Mutazyme can be from 40/1 to 1/400 or lower, preferably from 2.5/1 to 1/40. In a preferred embodiment of Mutazyme, the exo– Pfu DNA polymerase has a final concentration of 2.5 U/$\mu$l and PEF has a final concentration of 2 U/$\mu$l, therefore resulting in a ratio of 1.25/1. In a more preferred embodiment, recombinant untagged p45 (rp45) is used as the PEF to mix with the exo– Pfu DNA polymerase (commercially available from Stratagene, La Jolla, Calif. Catalogue # 600550).

V. PCR Mutagenesis by Mutazyme

The compositions comprising Mutazyme according to the subject invention may be used in various methods of synthesizing polynucleotides in essentially the same manner as the exo– Pfu DNA polymerase present in the subject composition. Typically, synthesis of a polynucleotide requires a set of synthesis primers, a synthesis template, polynucleotide precursors (e.g. dATP, dCTP, dGTP, and dTTP, also referred as dNTPs) for incorporation into the newly synthesized polynucleotide. Detailed methods for carrying out polynucleotide synthesis are well known to the person of ordinary skill in the art and can be found, for example, in Molecular Cloning second edition, Sambrook et al., Cold Spring Harbor Laboratory Press, Cold Spring Harbor, N.Y. (1989). Polymerase chain reaction (PCR) is one of the most well known methods for DNA synthesis, amplification and mutagenesis (Cadwell, R. C. and Joyce, G. F. 1992. Randomization of genes by PCR mutagenesis. PCR Methods Appl. 2:28–33; Leung, D. W., Chen, E., and Goeddel, D. V. 1989. A method for random mutagenesis of a defined DNA segment using a modified polymerase chain reaction. Technique 1:11–15). Mutazyme may also be used for other random mutagenesis methods well known in the art, such as primer extension or reverse transcription (Ausubel et al., John Weley & Sons, Inc., 1997, *Current Protocols in Molecular Biology*).

Conventional PCR mutagenesis methods employ Taq DNA polymerase, as it lacks proofreading activity and is inherently error prone. The process of PCR employs multiple cycles with a template denature step, a primer annealing step, and a polynucleotide synthesis step in each cycle. A PCR reaction mixture typically contains a nucleic acid template, a DNA polymerase, a suitable reaction buffer, a dNTP mix, and/or other additives.

A. Amount of Mutazyme in PCR Reaction

PEF enhances the performance of Pfu DNA polymerase when present at concentrations spanning a 10,000-fold range (0.09–900 U/100 $\mu$l) in the PCR reaction. In a preferred embodiment, this corresponds to 0.09–900 ng PEF per 100 $\mu$l reaction mixture. Preferably, the PEF concentration present in the PCR reaction is from 1 to 100 ng/100 $\mu$l.

B. PCR Parameters

Any PCR conditions which allow the amplification of nucleic acid template by Pfu DNA polymerase is encompassed by the subject invention. The PCR amplification is usually carried out in a 50 $\mu$l or 100 $\mu$l volume. In preferred embodiments, the PCR reaction mixtures comprise 1× Mutazyme reaction buffer, 200 $\mu$M each dNTP, 125 ng each primer, and 2.5 U Mutazyme DNA polymerase. The reactions are cycled in a RoboCycle® Gradient 40 Temperature Cycler (Stratagene), fitted with a hot top assembly. The following cycling parameters are employed: 1 cycle of 95° C. for 1 minute; 30 cycles of 95° C. for 1 minute, 55° C. for 1 minute, and 72° C. for 1 minute ($\leq$1 kb templates) or 1 minute per kb (>1 kb templates).

C. Reaction Buffer and dNTPs

Taq DNA polymerase needs a buffer with $Mn^{2+}$ and unbalanced dNTP concentration to be highly mutagenic. Polymerization is carried out under sub-optimal conditions in the presence of $Mn^{2+}$ and an unbalanced dNTP concentration, and PCR yield is reduced by more than two-fold (Melnikov, A. and Youngman, P. J. (1999) Random mutagenesis by recombinational capture of PCR products in *Bacillus subtilis* and *Acinetobacter calcoaceticus*. Nucleic Acids Res. 27(4):1056–1062).

Mutazyme has a 6-fold higher intrinsic error rate than Taq DNA polymerase. Therefore Mutazyme does not require mutagenic buffer conditions in order to perform error prone PCR. However, a mutagenic buffer (e.g., a buffer containing $Mn^{2+}$ or a buffer with an unbalanced dNTP concentration) may be used in the subject invention.

Buffers useful to the subject invention include any buffer compositions that allow the amplification of a nucleic acid template by Mutazyme. Preferably, the buffer contains $Mg^{2+}$ and a buffering component of either Tris or Tricine. Also preferably, the buffer has a pH range of from 7.5 to 9.2. More preferably, the buffer contains a component to enhance the yield of the amplified product, e.g., $(NH_4)_2SO_4$ and KCl. Other buffer components such as BSA, non-ionic detergent (e.g., Triton X-100, Tween 20, NP40) may be added to the buffer as long as the buffer provide the desired yield and mutation frequency for a given template.

Optimal PCR buffer allows Mutazyme to be a more robust polymerase. In a preferred embodiment, a universal Mutazyme PCR reaction buffer containing 20 mM Tris, 10 mM KCl, 10 mM $(NH_4)_2SO_4$, 2 mM $MgSO_4$, 100 µg/ml BSA, and 0.1% Triton X-100. In one embodiment, the pH of the Mutazyme PCR reaction buffer is 8.8. In another embodiment, the pH of the Mutazyme PCR reaction buffer is increased (e.g., pH 9.2) to achieve higher mutation frequencies.

In order to obtain high mutation frequencies (>6,000 mutations per $10^6$ base pair), Taq DNA polymerase requires the change of the one or more of the dNTP concentrations (e.g., increasing the concentration of dGTP). In contrast, Mutazyme generates a variety of mutation frequencies with equivalent amount of each of the dNTPs. Therefore, it's not required to increase one of the dNTP concentrations when a high mutation frequency is desired.

In a preferred embodiment, a final concentration of 200 µM of each dNTPs is used.

D. Target Nucleic Acid Template (Length, Source, and Yield)

Mutagenesis by Taq DNA polymerase requires the use of a suboptimal PCR reaction buffer comprising $Mn^{2+}$ and an unbalanced dNTP concentration and can only amplify nucleic acid less than 1 kb in length (Leung, D. W., Chen, E., and Goeddel, D. V. 1989. A method for random mutagenesis of a defined DNA segment using a modified polymerase chain reaction. Technique 1:11–15; Stemmer, W. P. 1994. DNA shuffling by random fragmentation and reassembly: in vitro recombination for molecular evolution. Proc. Natl. Acad. Sci. USA 91:10747–10751).

The PCR enhancing effect of PEF in Mutazyme allows the amplification of long or low copy number targets. Therefore lowering the template concentration may be used to achieve a desired high product yield with mutzyme, but not with Taq DNA polymerase. Mutazyme with exo– Pfu DNA polymerase (2.5U/µl) and PEF (2U/µl) significantly increases yields of PCR templates up to 10 kb. Mutazyme is capable of amplifying DNA fragment of 1 kb, 2 kb, 3 kb, 4 kb, 5 kb, 6 kb, 7 kb, 8 kb, 9 kb, 10 kb, or greater in length.

In one embodiment, Mutazyme efficiently amplifies a 10 kb lambda target from 10 pg of lambda DNA. In another embodiment, Mutazyme amplifies plasmid targets of 650 bp, 2.5 kb, and 4.5 kb. The PCR yield of these targets is higher than that generated by Taq or exo– Pfu DNA polymerase.

Mutazyme enhances the yield of PCR products using plasmid, lambda, and genomic DNA templates. Therefore, fewer PCR cycles or lower template concentrations could be used in Mutazyme containing amplifications. The PCR enhancing effect of PEF in Mutazyme also allows the amplification of highly complex targets. When exo– Pfu DNA polymerase is used in the absence of PEF, such targets are poorly amplified.

In one embodiment, a 5.2 kb target is successfully amplified from human genomic DNA by Mutazyme with relatively shorter extension time per kb template, compared to exo– Pfu DNA polymerase.

In a preferred embodiment of the subject invention, when a target is amplified from genomic DNA and low-to-medium mutation rates are desired, the target is first amplified with a high fidelity DNA polymerase (i.e., wild type Pfu). The amplified PCR product is then used as template for Mutazyme mutagenesis.

E. The Amount of Target Nucleic Acid Template and Mutation Frequencies

Mutazyme of the subject invention amplifies nucleic acid template more efficiently with less starting template concentration, compared to Taq and exo– Pfu DNA polymerases. Mutazyme is suitable for PCR amplification of DNA templates of 1 pg to 1 µg, preferably 10 pg to 100 ng. Nucleic acid concentration can be determined by methods well known in the art, for example, by measuring absorbencies at 260 nm.

Taq DNA polymerase mutagenesis relies on the presence of $Mn^{2+}$ and an unbalanced dNTP concentration to change the error rate of Taq DNA polymerase and therefore, the mutation frequency of the reaction. Sometimes, a range of different buffer conditions are required to vary the mutation frequency of the PCR reaction (Cline, J., Braman, J. C. and Hogrefe, H. H. 1996. PCR fidelity of Pfu DNA polymerase and other thermostable DNA polymerases. Nucleic Acids Res. 24:3546–3551). The subject invention provides a simple method of controlling mutation frequencies of target nucleic acid template by controlling the starting template concentration. In preferred embodiments of the invention, the mutation frequencies are proportional to the starting amount of nucleic acid templates.

Mutazyme has a high mutation frequency even with optimal buffers containing $Mg^{++}$ and balanced dNTPs. The error rate of exo–Pfu in cPfu buffer is $4.7 \times 10^{-5}$ which is about 6 fold higher than the error rate of Taq (Cline, J., Braman, J. C. and Hogrefe, H. H. (1996) PCR fidelity of Pfu DNA polymerase and other thermostable DNA polymerases.

Nucleic Acids Res. 24(18):3546–3551).

We use variation in number of target duplications to control the mutation frequency of the PCR reaction. Changing the ratio of PCR yield to starting amount of target alters the d value. The easiest way to increase d (and hence the mutation frequency) is to lower the starting amount of target. A single PCR amplification reaction may be used to achieve a d value of less than 20. In order to get values of d greater than 20 (greater than 10 mutations/kb), a second PCR is preferably performed.

To increase d values to greater than 20, one or more additional PCR reactions may be performed. The d values of the first and sequential PCRs are added together to get the overall d value. The actual corresponding mutation frequency to a d value may be determined by DNA sequencing of randomly selected clones of mutated product. In one embodiment, a second PCR is performed to achieve an overall d value of greater than 20. In another embodiment, a third PCR is performed which resulted in an overall d value of approximately 50. The mutation frequency observed after two or more sequential PCRs can be greater than 16 mutations/kb. It is possible, whenever desired, to perform more than three sequential PCRs. A mutation frequency of 29,200 mutations per $10^6$ base pair has been seen with six sequential rounds of PCR with Taq DNA polymerase (Shafikhani, S., Siegel, R. A., Ferrari, E. and Schellenberger, V. (1997) Generation of large libraries of random mutants in *Bacillus subtilis* by PCR-based plasmid multimerization. *Biotechniques* 23(2) 304–310). Since Mutazyme has higher error prone rate than Taq DNA polymerase, an even higher mutation frequency may be achieved.

Table 1 shows the range of calculated d values that can be achieved in theory by single or sequential PCR reactions using the indicated amounts of starting template and various projected product yields. In some embodiments, the d values shown in bold type are achieved experimentally where product yields of 0.1–7.5 μg/50 μl PCR were generated from 1 pg- 100 ng of target (FIG. 1). In one embodiment, a series of PCR reactions employing 1 pg, 10 pg, 1 ng, 10 ng or 100 ng of target DNA produced a range of d values from 5.6 to almost 17. The d value, and therefore, the mutation frequency, increases as the input DNA dropped from 100 ng (d=5.6) to 100 pg (d=15.6).

TABLE 1 d values at different product yield.

| start | 100 ng | 500 ng | 1 μg | 2.5 μg | 5 μg | 7.5 μg | 10 μg |
|---|---|---|---|---|---|---|---|
| 100 ng | 0 | 2.3 | 3.3 | 4.6 | 5.6 | 6.2 | 6.6 |
| 10 ng | 3.3 | 5.6 | 6.6 | 8.0 | 9.0 | 9.6 | 10 |
| 1 ng | 6.6 | 9.0 | 10 | 11.3 | 12.3 | 12.9 | 13.3 |
| 100 pg | 10 | 12.3 | 13.3 | 14.6 | 15.6 | 16.2 | 16.6 |
| 10 pg | 13.3 | 15.6 | 16.6 | 17.9 | 18.9 | 19.5 | 20 |
| 1 pg | 16.6 | 18.9 | 20 | 21.3 | 22.3 | 22.8 | 23.3 |
| 100 fg | 20 | 22.3 | 23.3 | 24.6 | 25.6 | 26.2 | 26.6 |
| Double PCR | | | 20 | | | 35 | |
| Triple PCR | | | 35 | | | 50 | |

The mutation frequencies can be divided into three ranges of numbers defining "Mutation Levels". The low mutation frequency PCRs use 10–100 ng (40–400 fmole) of target to achieve 1000–3,000 mutations/$10^6$ base pair. The medium mutation rate is achieved by using 10 pg to 10 ng (0.04–40 fmole) of target and gives a mutation frequency of 3000–7000 mutations/$10^6$ base pair. The high mutation rate is obtained using one or more additional PCR reactions, which give mutation frequencies of 7000–16000 mutations/$10^6$ base pair.

If one or more additional PCR reactions are performed subsequently, a portion of or the total of a preceding PCR amplified product may be used as the template of a subsequent PCR reaction. Preferably, a portion of the preceding PCR amplified product is used as the template of a subsequent PCR amplification. More preferably, less than 1/10, or 1/25, or 1/50 of the preceding PCR amplified product is used as the template of the subsequent PCR amplification. In one embodiment, the preceding PCR amplified product is purified before being used as template for a subsequent PCR amplification. In another embodiment, the preceding PCR amplified product is directly used as template for a subsequent PCR amplification without purification.

A lacZ mutagenesis assay may be used as control for the Mutazyme error prone PCR. Instead of sequencing to determine mutation frequency, mutations may be scored using the color-screening assay. Clones containing a mutation in lacZ that inactivates β-galactosidase activity produce white or colorless colonies on Xgal/IPTG plates. Wild type lacZ clones produce blue colonies on Xgal/IPTG plates.

E. Mutational Spectrum

Mutazyme generates similar mutation spectrum with different nucleic acid templates and the generated mutations are uniformly distributed on the nucleic acid templates. The mutational spectrum produced in the pH 9.2 buffer is similar to the spectrum generated in the pH 8.8 buffer with only slight differences. The frequency of incorporated mutations was comparable in the pH 8.8 buffer (6.96 mutations per kb) and the pH 9.2 buffer (6.58 per kb). The use of recombinant PEF protein rP45 does not alter mutation frequency or the mutational spectrum of exo–Pfu DNA polymerase.

One way of analyzing mutational bias is to use the ratio of transitions to transversions. Transition mutations are purine (A and G) to purine changes and pyrimidine (C and T) to pyrimidine changes. Transversions are purine to pyrimidine and pyrimidine to purine changes. There are eight possible transversions and four possible transitions. If a DNA polymerase lacks bias, the Ts/Tv ratio would be 0.5. The Ts/Tv ratio for Mutazyme is greater than 0.5, indicating that Mutazyme favors transitions over transversions. In one embodiment, Mutazyme generates a Ts/Tv ratio of greater than 1. Taq DNA polymerase also tends to make transition mutations more often than transversion mutations.

However, the types of mutations made by Mutazyme are different from the types of mutations produced by Taq DNA polymerase. While Mutazyme prefers to mutate G and C to A or T, Taq prefers to mutate A and T to G or C (Fromant, M, Blanquet, S. and Plateau, P. 1995. Direct random mutagenesis of gene-sized DNA fragments using polymerase chain reaction. *Anal. Biochem.* 224(1):347–353). Therefore, if the mutation bias is analyzed by a ratio of GC mutations to AT mutations, Mutazyme would have a GC/AT ratio of greater than 1 while Taq DNA polymerase would have a GC/AT ratio of less than 1.

In one embodiment, Mutazyme shows less bias with respect to Ts/Tv ratios at high mutation frequencies (>7 mutations/kb).

Taq DNA polymerase reaction buffer composition (e.g., $Mn^+$ concentration and the ratio of the dNTPs) has to be changed in order to increase the mutation frequency of the reaction. To further increase mutation frequencies to higher than 4.9–6.6 mutations per kb, one typically further increases the dGTP concentration. Selectively increasing the dGTP concentration can lead to changes in the mutational spectrum and further increases in the mutational bias of Taq (You and Arnold, supra). In contrast, because the Mutazyme reaction buffer does not need to be altered, the mutational spectrum does not change with different mutation frequencies.

As mentioned above, the ratio of GC/AT is another way to show mutational bias. For a DNA polymerase lacking bias, the ratio would be 1. The GC/AT ratio for Taq DNA polymerase ranges from 0.07 to 0.35, showing a tendency for Taq DNA polymerase to mutate from A or T to G or C (Table in Example 4) and from 0.52 to 0.73 (Shafikhani et al, 1997, supra). In contrast, the GC/AT ratio for Mutazyme in the pH 8.8 buffer is about 3–7, indicating that Mutazyme favors replacing G or C with A or T. Although Mutazyme preferentially introduces A and T mutations, the degree of bias (the distance from 1) is similar to that exhibited by the Taq DNA polymerase.

Furthermore, even though Mutazyme prefers to mutate C and G to A and T, it does make all possible nucleotide changes (A→G, G→A, T→C, C→T, G→T, T→G, C→A, A→C, A→T, T→A, G→C, and C→G). In contrast, Taq DNA polymerase makes no or only a few C→G plus G→C changes and G→T plus C→A changes all of which represent less than 3% of the total mutations made by Taq DNA polymerase. Mutazyme also generates fewer insertion and deletion mutations than Taq DNA polymerase does under low to medium mutation frequencies. Mutazyme, therefore, is less likely to produce nonfunctional proteins because an insertion or deletion often creates a frame shift which produces in inactive protein.

F. Mutazyme Generates Blunt Ends in the Amplified Mutant Product

Taq DNA polymerase is known to add dNTPs (primarily A) to the 3' end of PCR products, while Pfu creates blunt ends (Hu, G. (1993) DNA polymerase-catalyzed addition of nontemplated extra nucleotides to the 3' end of a DNA fragment. *DNA Cell Biol* 12(8):763–770). Because Mutazyme lacks 3'–5' exonuclease activity, it is not obvious whether Mutazyme will produce PCR products with blunt ends or with overhangs. Mutazyme is tested for extension activity using a blunt ended oligo duplex and the amplified product contains blunt ends.

VI. PCR Mutagenesis Using Mutazyme and Another exo- DNA Polymerase in Combination Every polymerase will produce a unique mutation spectrum (Keohavong, P., Ling, L., Dias, C. and Thilly, W. G. (1993) Predominant mutations induced by the *Thermococcus litoralis*, Vent polymerase during DNA amplification in vitro. *PCR Methods Applic.* 2:288–292; Shafikhani, et al., 1997, Generation of large libraries of random mutants in *Bacillus subtilis* by PCR-based plasmid multimerization, Biotechniques 23:304–310).

Nucleic acid mutant libraries may be made by PCR mutagenesis using a combination of two or more error-prone DNA polymerase. The DNA polymerases can be selected based on the desired mutation spectrum of the library and the mutational bias of a given DNA polymerase. For example, Taq DNA polymerase tends to mutate A and T sites, whereas Mutazyme tends to mutate G and C sites. The amino acid changes in a gene are likely to be quite different for PCR performed with Mutazyme than with Taq. A combination of the two DNA polymerases in PCR mutagenesis may give a near uniform mutational spectrum.

Preferably, the DNA polymerases used are exo- DNA polymerases. More preferably, one of the exo- DNA polymerases is exo- Pfu DNA polymerase.

If the selected DNA polymerases used have compatible reaction buffers and amplification parameters, one PCR reaction can be carried out with all DNA polymerases in one reaction mixture. By "compatible", it refers to reaction buffers or amplification parameters which allow the amplification of the template by all selected DNA polymerases. In one embodiment, PCR mutagenesis is carried out with exo- Pfu DNA polymerase and Taq DNA polymerase by incubating a nucleic acid template, two PCR primers, and the two DNA polymerase under the conditions which permit the amplification of the template by both DNA polymerases.

Any PCR reaction mixture and parameters may be used as long as it allows the amplification of the template by both DNA polymerases. Certain buffer compositions may be preferable to increase the mutation frequency for one or both DNA polymerases. For example, a change in pH, dNTP ratios, $Mg^{2+}$ concentration, and the inclusion of $Mn^{2+}$ can all alter mutation frequency. In a preferred embodiment, the PCR buffer contains $Mg^{2+}$ and a buffer component with a pH range of from 7.5 to 9.2. Components such as KCl, $(NH_4)_2SO_4$, BSA, non-ionic detergent, as described herein, may be added if desired. The reaction mixture may contain $Mn^{2+}$ and an unbalanced dNTP concentration (e.g., when Taq DNA polymerase is one of the polymerases used). By "unbalanced dNTP concentration", it means that one or more of the four dNTPs have concentrations different from the other dNTPs.

When a compatible reaction buffer or amplification parameters are not available, PCR reactions may be carried out sequentially with one DNA polymerase in each PCR reaction under its optimal PCR conditions. For example, exo- Pfu may be inefficient in buffer containing high amount of $Mn^{2+}$(>100 $\mu$M). So if Taq DNA polymerase is also used and a mutagenic buffer containing $Mn^{2+}$ is desired, the PCRs may be done separately and then combined or performed as two sequential PCRs.

The use of other mutagenic DNA polymerases may overcome problems of buffer incompatibility. For example, Mutazyme could be used with a DNA polymerase like UlTma, which has a high mutation frequency in the absence of manganese. Another possibility is exo-JDF3 (related to exo- Pfu). This DNA polymerase can be used in PCR in the presence of 0.5 mM $MnCl_2$ (0 mM $Mg^{++}$) and therefore could be used with Taq under mutagenic buffer conditions.

Preferably the DNA polymerase to use with exo- Pfu is another thermosatble polymerase. Preferably, the polymerase used in combination with exo- Pfu is naturally devoid of proofreading activity (e.g., thermostable eubacterial Family A DNA polymerases: e.g., Taq, Tth). In a preferred embodiment, Taq or Tth DNA polymerase is used in combination with exo- Pfu DNA polymerase in a buffer lacking $Mn^{2+}$ and unbalanced dNTPs. The error-prone rate of Taq DNA polymerase is increased by using one or more conditions selected from the group consisting of: increasing dNTP concentration, increasing $Mg^{2+}$ concentration (in excess over dNTPs), increasing pH, and using prolonged extension times and high enzyme amounts (Ling, L. L., Keohavong, P, Dias, C., and Thilly, W. G. (91) PCR Methods Appl. 1:63–69; Eckert, K. A. and Kunkel, T. A. (91) PCR Methods Appl. 1:17–24; Eckert, K. A. and Kunkel, T. A. (90) Nucl. Acids Res. 18:3739–44). The use of these conditions to decrease the fidelity of Taq, may provide suitable reaction conditions for a mix of exo–Pfu and Taq DNA polymerase so to avoid the use of $Mn^{2+}$ which significantly inactivates exo- Pfu DNA polymerase.

Other DNA polymerase that may be used in combination with exo- Pfu DNA polymerase include exo- archaeal DNA polymerases, with point mutations in the 3'–5' exo domain that eliminate exo activity; e.g., exo- JDF-3, Exo- Tli (Exo- Vent, New England Biolabs), Exo- P GB-D (Exo- Deep Vent, New England Biolabs).

There are other known proofreading archaeal DNA polymerases which could be make exo- by point mutagenesis; e.g., DNA polymerases from Thermococcus sp. KOD, *Thermococcus gorgonarius, Thermococcus aggregans, Pyrolobus fumarius*.

An additional group of DNA polymerase that may be used in combination with exo- Pfu DNA polymerase include polymerases modified to have reduced exonuclease activity. By "reduced exonuclease activity", it means that the modified polymerase has a exonuclease activity less than its wild type enzyme. Useful DNA polymerases with reduced exonuclease activities include N-terminally truncated eubacterial (Klenow-like fragments); UlTma (derived from *Thermotoga maritima* DNA polymerase). There are other known proofreading eubacterial DNA polymerases which could be make exo reduced by N-truncation; e.g., DNA polymerases from *Thermotoga neopolitana*. Another type of exo reduced DNA polymerase is an archaeal DNA polymerase with conservative point mutations in the 3'–5' exo domain; e.g., 9° Nm DNA polymerase (New England Biolabs).

PEF also enhances yields of PCR products obtained with a mixture of exo- Pfu DNA polymerase and Taq DNA polymerase. PEF can be also used for mixtures comprising exo- Pfu and other exo- DNA polymerase than Taq DNA polymerase.

PEF can be also used with exo–JDF3, either alone or in a mixture comprising exo- JDF3 and other exo–DNA polymerases.

VII. Mutant Nucleic Acid Library

The subject invention provides mutant libraries made by Mutazyme PCR amplification which have less or a different mutational bias than those generated by Taq DNA polymerase.

As described herein, both Taq DNA polymerase and Mutazyme generate a Ts/Tv ratio of greater than 1, therefore tend to make transition mutations more than transversion mutations. However, Taq DNA polymerase has a tendency to mutate A or T nucleotide (GC/AT<1), while Mutazyme has a tendency to mutate G or C nucleotide (GC/AT>1).

Furthermore, even though Mutazyme prefers to mutate C or G to A or T, it does make all possible nucleotide changes (A→G, G→A, T→C, C→T, G→T, T→G, C→A, A→C, A→T, T→A, G→C, and C→G). In contrast, Taq DNA polymerase makes no or only a few C→G plus G→C changes and G→T plus C→A changes.

Therefore the library generated using Mutazyme would contain unique mutations compared to that generated by Taq DNA polymerase. In addition, the library generated by Mutazyme would be more represented in mutations at Gs and Cs compared to Taq libraries.

Since each DNA polymerase may have its unique bias in generating mutations, libraries according to the invention can be generated, as described herein, by using Mutazyme and one or more other exo− DNA polymerases to create libraries with less bias and greater diversity compared to one generated with one DNA polymerase. For example, Taq DNA polymerase is skewed to favor mutations at AT base pairs while exo− Pfu DNA polymerase favors GC mutations. In one embodiment, a library is generated using a combination of Taq and exo− pfu DNA polymerases by a first PCR mutagenesis with Taq DNA polymerase in a buffer containing $Mn^{2+}$ and unbalanced dNTPs followed by a second PCR where a portion of the first amplification reaction is subject tofurther PCR mutagenesis by Mutazyme in the pH 8.8 buffer. In another embodiment, PCRs are carried out with a blend of two DNA polymerases.

When two DNA polymerases are used to generate a mutant library, a first PCR reaction can be performed with a first DNA polymerase and a second PCR reaction with a second DNA polymerase can be performed using a portion of the first PCR reaction.

In some embodiments of the invention, the libraries are generated using one or more additional PCR amplification reactions to increase the mutation frequencies of the libraries as described herein.

The use of PEF in Mutazyme increases the efficiency of the PCR reaction and therefore provides higher product yield than amplifications without PEF. High PCR yield provided by Mutazyme is also desired for random mutagenesis in order to construct libraries that are as large and representative as possible.

VIII. Kits

The invention is intended to provide novel compositions and methods for PCR mutagenesis as described herein. The invention herein also contemplates a kit format which comprises a package unit having one or more containers of the subject composition and in some embodiments including containers of various reagents used for polynucleotide synthesis, including synthesis in PCR. The kit may also contain one or more of the following items: polymerization enzymes, polynucleotide precursors, primers, buffers, instructions, and controls. The Kits may include containers of reagents mixed together in suitable proportions for performing the methods in accordance with the invention. Reagent containers preferably contain reagents in unit quantities that obviate measuring steps when performing the subject methods. One kit according to the invention also contains a DNA yield standard for the quantitation of the PCR product yields from a stained gel.

In one preferred embodiment, the polymerase enzyme in the kit is Mutazyme. In another preferred embodiment, the kit comprises both Mutazyme and Taq DNA polymerase.

Preferably, the kit contains a universal PCR reaction buffer without the addition of $Mn^{2+}$. Also preferably, the kit contains equal molar concentration of each dNTPs. Still preferably, the PCR reaction is set up like a normal PCR reaction with the only variable in the reaction being the amount of starting template which controls the mutation frequencies in the final PCR product.

In one embodiment, three levels of mutagenesis: low (1–3,000 mutations per $10^6$ kb), medium (3,000–7,000 mutations per $10^6$ kb) and high (7,000–16,000 mutations per $10^6$ kb), are obtained by using 10–100 ng of target, 10 pg–10 ng of target, and an additional PCR reaction respectively. This may be achieved by first diluting the DNA template into series concentrations (e.g., 10 pg/$\mu$l, 100 pg/$\mu$l, 1 ng/$\mu$l, 10 ng/$\mu$l, 100 ng/$\mu$l, etc.). 1 $\mu$l of the template of each concentration can be used in the PCR reaction mixture containing a suitable PCR buffer (e.g., the pH 8.8 buffer). The PCR may be performed under parameters known in the art (Cline et al., 1996, *Nucleic Acids Research*, 24:3546). In one embodiment, the PCR is set up in a mixture containing 2.5 U Mutazyme, 200 $\mu$M each of dNTPs, two primers (100–250 ng each) in a final concentration of 50 $\mu$l.

According to the subject invention, a kit may also contain reagents required for a lacZ mutagenesis assay which may be used to verify the quality of the Mutazyme error prone PCR kit.

Other PCR additives such as DMSO may be added to kits to improve product yields when amplifying targets that have high GC content or difficult secondary structures (Landre et al., 1995; Berger 1994; Sun et al., 1993).

EXAMPLES

The examples below are non-limiting and are merely representative of various aspects and features of the subject invention.

Example 1

Template Preparation

A plasmid containing the lacZ target sequence was used as a template for Mutazyme PCR mutagenesis. The plasmid was constructed by subcloning a 650 bp lacZ insert into EcoRI and XhoI sites in pBC SK+ vector, resulting in new vector pBC SK+-lacZ, which is chloramphenicol resistant.

Complete sequence of lacZ insert (SEQ ID NO:1) including LIC (ligation independent cloning) and restriction sites (underlined) is shown below (LIC Primers shown in Italics and start of lacZ shown in bold, SEQ ID NO:2 for the forward primer, as shown in italics at the beginning of SEQ ID NO:1 and SEQ ID NO:11 for the sequence complementary for the reverse primer as shown in italics at the end of SEQ ID NO:1):

(Xho I)
<u>CTCGA</u>GGAACAAGACCCG *TTACTAGTAC*TTATCCCTGATTCTGTGGATAA

CCGTATTACCGCCTTTGAGTGAGCTGATACCGCTCGCCGCAGCCGAACGA

CCGAGCGCAGCGAGTCAGTGAGCGAGGAAGCGGAAGAGCGCCCAATACGC

-continued

```
AAACCGCCTCTCCCCGCGCGTTGGCCGATTCATTAATGCAGCTGGCACGA

CAGGTTTCCCGACTGGAAAGCGGGCAGTGAGCGCAACGCAATTAATGTGA

GTTAGCTCACTCATTAGGCACCCCAGGCTTTACACTTTATGCTTCCGGCT

CGTATGTTGTGTGGAATTGTGAGCGGATAACAATTTCACACAGGAAACAG

CTATGACCATGATACGCCAAGCGCGCTCACTGGCCGTCGTTTTACAACGT

CGTGACTGGGAAAACCCTGGCGTTACCCAACTTAATCGCCTTGCAGCACA

TCCCCCTTTCGCCAGCTGGCGTAATAGCGAAGAGGCCCGCACCGATCGCC

CTTCCCAACAGTTGCGCAGCCTGAATGGCGAATGGGACGCGCCCTGTAGC

GGCGCATTAAGCGCGGCGGGTGTGGTGGTTACGCGCAGCGTGTCGACGTT

AA CTTGTCGTCGTC GAATTC
                (EcoR I)
```

The plasmid concentration was determined by reading an OD at 260 nm. The plasmid was then diluted to 100 ng/μl. Sequential ten fold dilutions of this plasmid were done to generate the other concentrations used in the assay below.

Mutazyme Error Prone PCR of pBC SK$^+$-lacZ Plasmid

The pBC SK$^+$-lacZ plasmid was used as template for Mutazyme mediated PCR mutagenesis.

100 ng, 10 ng, 1 ng, and 100 pg of lacZ DNA (contained within the pBC SK+-lacZ plasmid) were used in PCR amplifications. The PCR reactions were set up in a final volume of 50 μl containing 1× pH 8.8 buffer (20 mM Tris, 10 mM KCl, 10 mM AmSO$_4$, 2 mM MgSO$_4$, 100 μg/ml BSA, and 0.1% Triton X-100), 200 μM of each dNTPs, and 250 ng each primer (forward XhoI end 5' GGA ACA AGA CCC GTT ACT AGT ACT (SEQ ID NO:2); reverse EcoRI end 5' GAC GAC GAC AAG TTA ACG TCG ACA (SEQ ID NO:3)), 2.5U Mutazyme DNA polymerase, 1 μl template (100pg/μl-100 ng/μl), and 42.1 μl water (50 μl final).

The PCR was performed in a Robocycler 40 with hot top with the following parameters: step one: 95° C. 1 min, step two 95° C. 1 min (denaturation), step three 55° C. 1 min (annealing), step four 72° C. 1 min (extension), with steps two to four repeated 30 times.

The amplified PCR product was analyzed on an agarose gel. The 650 bp band corresponding to lacZ insert was cut out of the gel and purified with the Strataprep gel extraction kit (Stratagene, cat #400766). 1 μl of the purified PCR product was used to clone into the Affinity™ LIC vector (Cat#214310) following the product manual through the transformation step using Solopack™ Gold cells (Cat #230350). The transformation was plated on Xgal/IPTG/ LB/Amp plates.

d values were calculated as d=log (A/B)/log2, wherein A is the yield of amplified mutated produce, B is the amount of start nucleic acid template. B (10 pg to 100 ng) is calculated as 16% of the total amount of template DNA added to the reaction (62.5 pg to 625 ng) because the target lacZ insert (650 bp) is only 16% of the pBC SK$^+$-lacZ length (4.05 kb).

PCR Yield Quantitation

To examine the yield of amplified product, 10 μl of each PCR reaction was analyzed on a 1% agarose gel. A DNA standard at concentrations of 100 ng and 2 μg was also loaded. PCR product yield was compared to the DNA standard. This can be done by eye, or more accurately, using the Eagle Eye II Still Video System to quantitate (Stratagene, Cat. #401304). The 10 μl of each PCR reaction analyzed must contain 100 ng to 2 μg DNA in order to obtain an accurate quantitation. For the entire 50 μl reaction, there was a yield of between 500 ng and 10 μg.

lacZ Color Screening Assay

The mutation frequency of each PCR amplified product was first measured by a color-screening assay as follows.

The amplified lacZ fragment was cloned into an ampicillin resistant vector, Affinity™ LIC vector. If there was carry over of the pBC SK$^+$-lacZ plasmid (chloramphenicol resistant) to the transformation step, it would not be seen as background.

LB/Amp plates were prewarmed at 37° C. Appropriate amount of top agar was melted. 3 mls top agar was used for each 75 mm plate and cooled to 50° C. in a water bath. To 100 mls of melted top agar, 150 μl 1M IPTG (dissolved in water) and 150 mg Xgal in 540 μl DMF were added. The plates were cooled and then chilled at 4° C. 25 μl and 175 μl of each transformation were plated and grow overnight at 37° C. If the blue colonies were pale when the plates were taken out of the incubator, the plates were allowed to sit at RT or 4° C. for several hours before counting. Blue colonies contain wild type copy of the lacZ gene and white colonies contain mutations in lacZ gene that inactivate β-galactosidase activity. Pale blues colonies were counted as blue colonies. At least 100 colonies from each transformation were counted to get an accurate count of mutation frequency. Total number of colonies and percent mutant (white) colonies were recorded.

Sequencing

The mutation frequency and mutational spectrum produced were also determined by DNA sequencing. PCR reactions were cloned into the Affinity vector and annealing products transformed into Solopack™ Gold cells. Individual colonies were picked and resuspended in 200 μl TE. One microliter of each suspension was added to a 50 μl PCR reaction with Herculase™ enhanced DNA polymerase (Cat #600280). The clones were amplified with one gene specific primer (EcoRI end primer for lacZ) and one vector specific primer (Affinity new C primer 5'GCT AGT TAT TGC TCA GCG GTG (SEQ ID NO:4)). PCR products were purified with the Strataprep kit (cat#400771). Sequencing was performed by Sequetech using a nested gene specific primer (XhoI end primer for lacZ).

Figure 3:
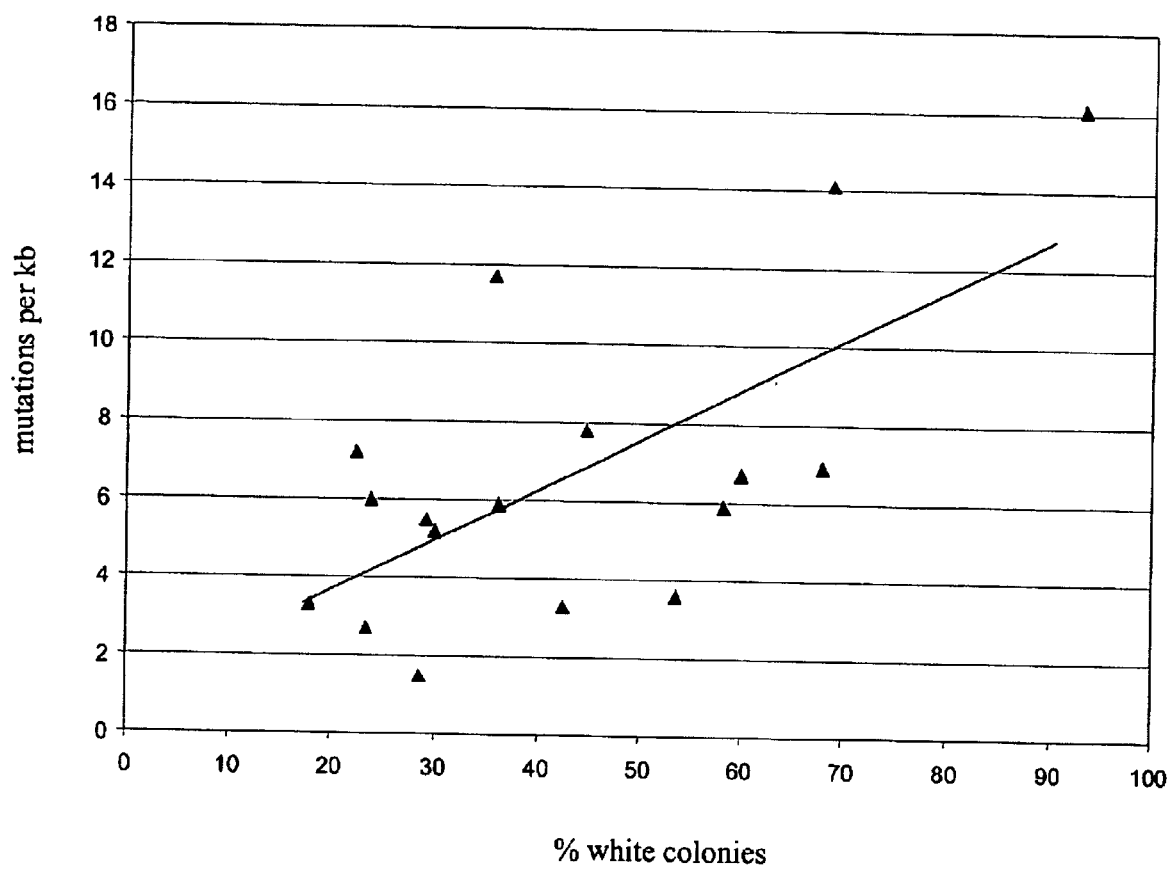
FIG. 3 shows the relationship between phenotype (percent of white colonies) and genotype (mutation frequency) in a lacZ assay as described in Example 1.

FIG. 3 show the relationships between mutant phenotype (percent white colonies) and genotype (mutation frequency). Clones from each PCR reactions were sequenced. DNA sequences for each template concentration were analyzed to calculate the mutation frequency. For each lacZ reaction, a total of 0.8–5.3 kb of DNA sequence from 2–10 random clones was analyzed. For the RT and GFP reactions, 3.2 kb (6 clones) and 4.5 kb (6 clones) were analyzed respectively.

Figure 4:
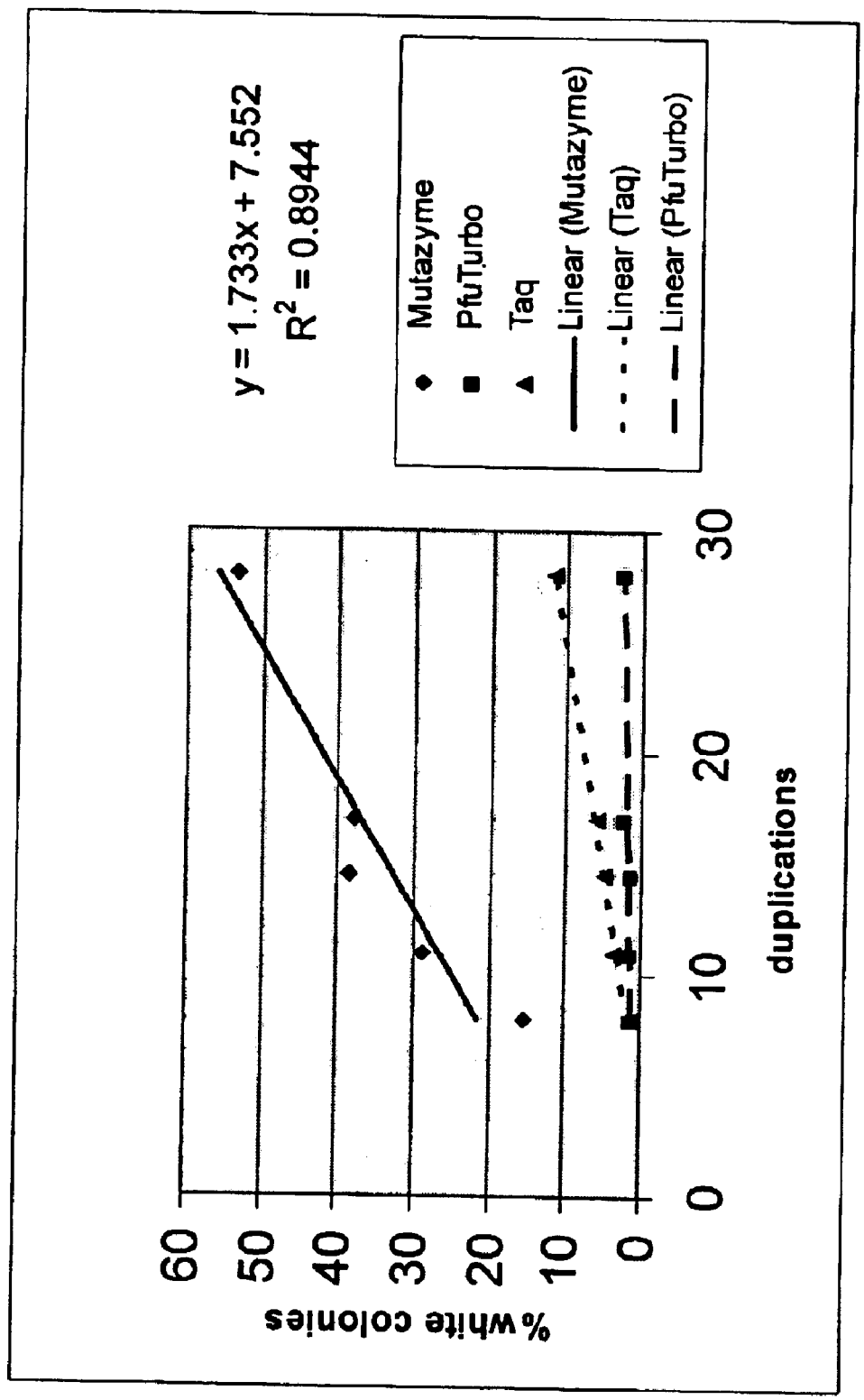
FIG. 4 shows a lacZ assay with Mutazyme, PfuTurbo and Taq. Amplification of 100 ng, 10 ng, 1 ng, 100 pg, and a double PCR from lacZ was performed as described in Example 1. Mutazyme and PfuTurbo were done in cPfu buffer. Taq2000 was done in standard Taq buffer with balanced dNTPs. All polymerases were 2.5 units/reaction. The d value was determined from the PCR yield from an Ethidium Bromide stained gel using the Eagle Eye concentration program and the equation on page 1. The % white colonies was determined with the color-screening assay. At least 100 colonies were counted from each data point. The equation shown is for the Mutazyme trendline.
Figure 5:
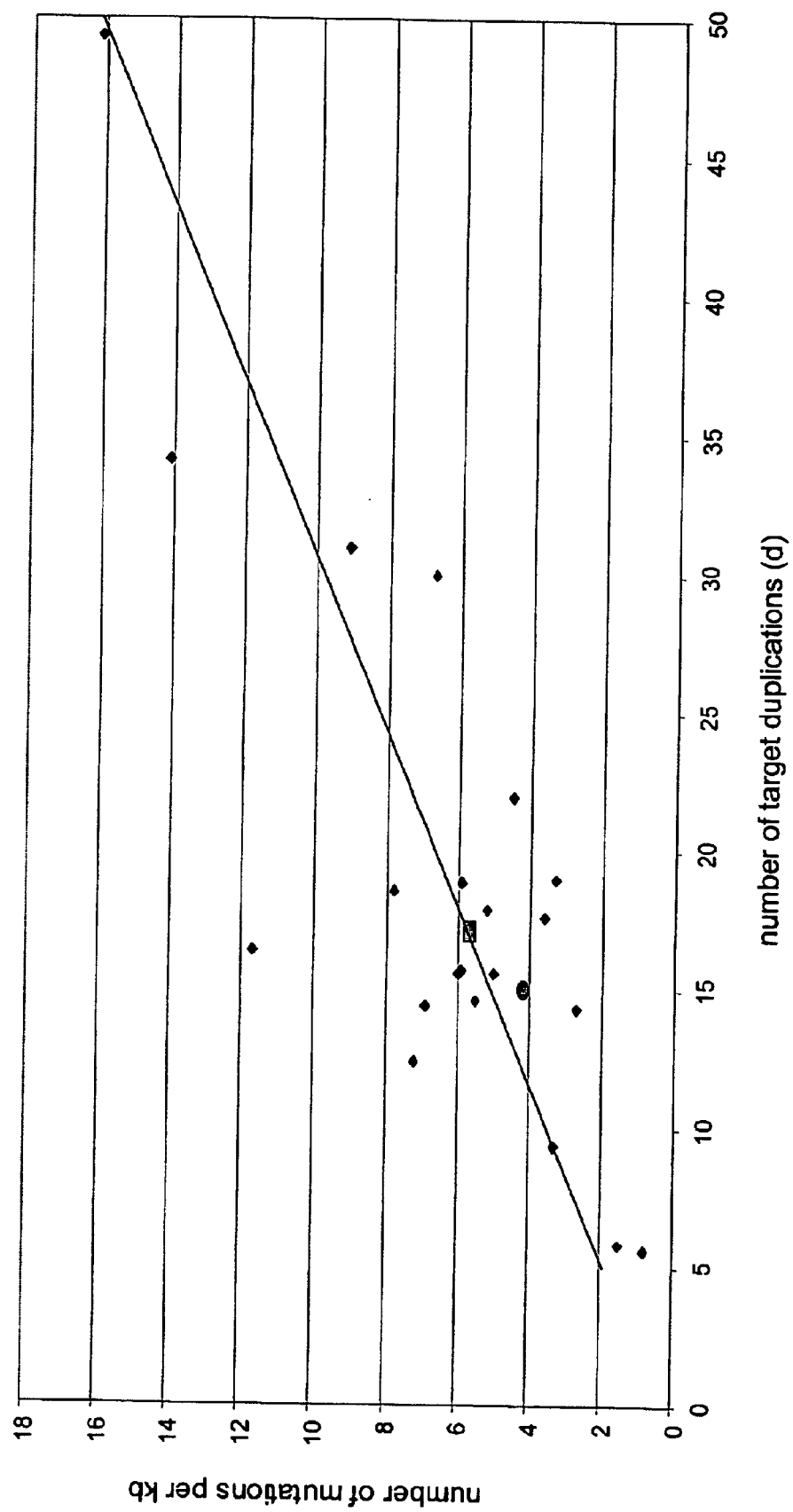
FIG. 5 shows the relationship between duplications (d value) and mutation frequency. All reactions were Mutazyme in cPfu buffer. Conditions were as described in Example 1. The value for d was calculated by estimating PCR yield from an EtBr stained agarose gel and then using the equation shown on page 1. The value for mut/kb was determined by sequencing. One data point (rectangle) is amplification of 10 pg MMLV-RT and 3.2 kb of sequence from 6 clones. Amplification of 100 pg GFP (circle) is data from 4.5 kb sequence of 6 clones. The rest of the data points (diamonds) are from amplification of 1 pg- 100 ng of lacZ. Each point is 0.8–5.3 kb of sequence from 2–10 clones. The trendline and equation shown are determined by the Excel program.

As expected, there was a direct relationship between percent white colonies and number of mutations determined by DNA sequencing (FIG. 4). Also as expected, mutation frequency increased with increasing d value (FIG. 5). The equation of the line relating mutation frequency (mut/kb) to d value was calculated as: mut/kb=0.31d+0.41 with a correlation coefficient of 0.65.

Example 2

The mutation spectrum of Mutazyme was examined, as well as the effect of buffer pH on Mutazyme mutation spectrum. The PCR reactions were performed using pBC SK$^+$-lacZ as template (10–100 pg plasmid DNA) as described in Example 1. Table 2 shows the mutation frequency and spectrum of Mutazyme in the pH 8.8 buffer and the pH 9.2 buffer. Over 20 kb of sequence from at least 40 lacZ clones is analyzed for each buffer condition.

TABLE 2

Mutation frequency and spectrum of Mutazyme with different buffer conditions.

|  |  | pH 8.8 | | pH 9.2 | |
|---|---|---|---|---|---|
|  |  | # of Mutations | % total Mutations | # of Mutations | % total Mutations |
| Transitions | A→G | 10 | 3.8 | 4 | 2.7 |
|  | G→A | 61 | 23.4 | 32 | 21.3 |
|  | T→C | 17 | 6.5 | 3 | 2.0 |
|  | C→T | 53 | 20.3 | 42 | 28.0 |
| Transversions | G→T | 32 | 12.3 | 10 | 6.7 |
|  | T→G | 9 | 3.4 | 3 | 2.0 |
|  | C→A | 20 | 7.7 | 14 | 9.3 |
|  | A→C | 2 | 0.8 | 2 | 2.0 |
|  | A→T | 16 | 6.1 | 9 | 6.0 |
|  | T→A | 13 | 5.0 | 4 | 2.7 |
|  | G→C | 12 | 4.6 | 12 | 8.0 |
|  | C→G | 11 | 4.2 | 5 | 3.3 |
| Insertions |  | 2 | 0.8 | 8 | 5.3 |
| Deletions |  | 3 | 1.1 | 2 | 2.0 |
| Ts/Tv |  | 1.2 |  | 1.4 |  |
| kb analyzed |  | 37.5 |  | 22.8 |  |

The mutational spectrum produced in the pH 9.2 buffer is similar to the spectrum generated in the pH 8.8 buffer with only slight differences. The pH 9.2 buffer did slightly increase the mutation frequency (6.6 mut/kb) as compared to the pH 8.8 buffer (6.0 mutations/kb) using the lacZ test system.

Example 3

Two other genes were also used as mutational targets for Mutazyme PCR mutagenesis.

The 2.5 kb gene encoding RNaseH-MMLV-RT was amplified from plasmid pDION containing RT DNA with the following primers:

```
RT N terminus
5'GAC GAC GAC AAG ATG ACC CTA AAT ATA GAA GAT
(SEQ ID NO:5)

RT C terminus
5'GGA ACA AGA CCC GTC AAG CTT TGC AGG TCT CAG TG
(SEQ ID NO:6)
```

The PCR products were cloned into the Affinity™ LIC vector and the annealed products transformed into XL10 Gold. The inserts from several clones were amplified, and the PCR products sequenced. 600 bp was sequenced from each of Ten MMLV-RT clones with the two above primers.

A 720 bp gene encoding humanized *Renilla reniformis* green fluorescent protein (GFP) was the third mutagenesis target. 1 ng of plasmid (about 0.1 ng of target) was amplified from template with the primers:

```
5' Retro primer    5'GGC TGC CGA CCC CGG GGG TGG
                   (SEQ ID NO:7)

3' pFB primer      5'CGA ACC CCA GAG TCC CGC TCA
                   (SEQ ID NO:8)
```

The PCR products were cloned into the EcoR1/Xho1 sites of the pFB retroviral vector (CAT#217563). Strataprep minipreps were performed for six GFP clones. 720 bp from each clone was sequenced with the above primers.

All PCRs were performed in a Robocycler 40 with hot top. Cycling parameters were as described in the lacZ assay except that 2.5 minute extension times were used for the RT gene.

Data obtained in seven different experiments were shown in FIG. 5. These data were generated from 23 different PCR reactions employing varying amounts of input template. Mutation frequencies were measured using lacZ (diamond), MMLV RT (rectangle), or GFP (circle) as the mutational target gene. Two to ten clones from each PCR reaction were sequenced. A total of 800–5250 bases of DNA sequence for each data point were analyzed to calculate the mutation frequency.

As expected, mutation frequency increased with increasing d value. The mutation frequencies obtained using the MMLV-RT target gene (d=17) and the GFP target gene (d=15) were consistent with the mutation frequencies observed using lacZ and similar template duplications. The equation of the line relating mutation frequency (mut/kb) to d value was calculated as: mut/kb=0.31d+0.41 with a correlation coefficient of 0.65.

Table 3 shows the spectrum of mutations produced using the reverse transcriptase (RT) and GFP genes (in the pH 8.8 buffer), which is imilar to that generated using the lacZ gene (Table 2).

TABLE 3

Mutation frequency and spectrum of Mutazyme

|  |  | RTpH 8.8 % total Mutations | GFPpH 8.8 % total Mutations |
|---|---|---|---|
| Transitions | A→G | 3.1 | 10 |
|  | G→A | 21.9 | 10 |
|  | T→C | 6.3 | 5 |
|  | C→T | 9.4 | 25 |
| Transversions | G→T | 9.4 | 15 |
|  | T→G | 6.3 | 0 |
|  | C→A | 0 | 0 |
|  | A→C | 0 | 0 |
| Transversions | A→T | 6.3 | 0 |
|  | T→A | 18.8 | 10 |
|  | G→C | 9.4 | 10 |
|  | C→G | 6.3 | 5 |
| Insertions |  | 0 | 0 |
| Deletions |  | 3.1 | 10 |
| Ts/Tv |  | 0.7 | 1.5 |
| kb analyzed |  | 4.8 | 4.5 |

Example 4

The mutation spectrum of Mutazyme from Table 2 is compared to that generated by Taq DNA polymerase using the Clontech Diversify™ Random Mutagenesis kit (Clontech, Cat. #k1830-1) (Table 4). Mutazyme PCR mutagenesis was performed using lacZ DNA template as described in Example 1.

TABLE 4

Comparison of Mutation spectra generated by Mutazyme and Taq DNA polymerase

|  |  | Taq DNA Pol.* Condition 1 low mutagenic rate | Taq DNA Pol.* Condition 2 medium mutagenic rate | Taq DNA Pol.* Condition 3 high mutagenic rate | Mutazyme pH 8.8 buffer |
|---|---|---|---|---|---|
|  | Ts/Tv | 0.9 | 1.3 | 3.9 | 1.2 |
|  | GC/AT | 0.13 | 0.34 | 0.07 | 5 |
| Transitions | A→G, T→C | 33.3 | 42.7 | 74.0 | 10.3 |
|  | G→A, C→T | 8.3 | 11.5 | 4.9 | 43.7 |
| Transversions | A→T, T→A | 16.7 | 26.0 | 13.8 | 11.1 |
|  | A→C, T→G | 27.8 | 8.3 | 4.1 | 4.2 |
|  | G→C, C→G | 0 | 0 | 1.6 | 8.8 |
|  | G→T, C→A | 0 | 6.3 | 0.8 | 20.0 |
| Insertions |  | 2.8 | 2.1 | 0 | 0.8 |
| Deletions |  | 11.1 | 3.1 | 0.8 | 1.1 |
| Mut/kb |  | 2 | 4.6 | 8.1 | 1–20** |

*The Taq data in Table 4 was obtained from Clontech's product literature on the Diversify kit (Diversify ™ PCR Ransom Mutagenesis Kit User Manual PT3393-1, catalog # K1830-1).
**Mut/kb varies with d value.

The types of mutations made by Mutazyme are different from the types of mutations produced by Taq DNA polymerase. Bias in mutation spectra can be analyzed by assessing the Ts/Tv and GC/AT ratios. Both Taq and Mutazyme tend to make transition mutations more often than transversion mutations (with Ts/Tv greater than 0.5). However, Mutazyme preferentially mutated G or C nucleotides (GC/AT being 5) while Taq DNA polymerase preferentially mutated A or T nucleotides GC/AT average 0.13).

Similar to Taq DNA polymerase, Mutazyme generated mutations are uniformly distributed on the nucleic acid template of mutations.

The mutation frequencies of Mutazyme were also compared to PfuTurbo (Stratagene, Cat. #600252) and Taq2000 (Stratagene, Cat. #600196) using the lacZ assay. PCR with Mutazyme was performed as described in Example 1, and PCR reactions for the other two enzymes were performed as recommended in the product manual. Each polymerase was used at 2.5 units/50 µl PCR reaction.

FIG. 4 shows a comparison of percent white (mutant) colonies vs duplications (d) for Mutazyme, PfuTurbo, and Taq (in Mg++buffer). For each polymerase four reactions consisting of a single round of PCR (d=8,11,15,17) and one reaction consisting of two sequential PCRs (d=28) were performed. As expected, the number of mutant clones is directly related to d value for all three polymerases tested. The plot for Mutazyme, which should have the highest mutation frequency, exhibited the greatest slope. PfuTurbo, which should have the lowest mutation frequency, produced a level of errors at or near background until d=17. The plot for Taq is intermediate between the two as expected (error rates: Pfu $1.3 \times 10^{-6}$, Taq $8 \times 10^{-6}$, Mutazyme $47 \times 10^{-6}$ mutations/bp/d). Although the graph does not give actual values for mutation frequency, it does show that Mutazyme is error prone and produces an increase in number of mutant clones as d increases.

The addition of PEF in the mutazyme did not alter the mutation frequency of exo- Pfu DNA polymerase.

Example 5

To obtain a mutation frequency greater than 10 mutations/kb or a d value greater than 20, one or more additional PCR reactions were employed.

A portion of the first PCR reaction was re-amplified. One microliter of the first PCR (either the products from the 1 ng or the 100 pg reaction above) was diluted 1:1000 in TE and 1 µl of the dilution was added to a second 50 µl PCR reaction. The reaction conditions were the same as described in Example 1. A third PCR can also be carried out using the re-amplification products as template by diluting a portion of the second PCR 1:1000 in TE and then amplifying 1 µl in a third 50 µl PCR reaction.

Table 5 lists the range of mutation frequencies expected for the indicated amount of starting template and assuming product yields of 0.5–10 µg/50 µl reaction. These values were calculated from the equation MF=0.31d+0.41. If the first PCR has ad value of about 17 (mutation frequency of 6 mut/kb) and the second PCR has a d value of 18. The total d value is 35. The mutation frequency, as determined by DNA sequencing of randomly selected clones, was found to be 14 mut/kb.

TABLE 5

Mutation/kb

| Start | Start fmole | Calculated mut/kb | Actual mut/kb | Experimental Average mut/kb | Mutation Level |
|---|---|---|---|---|---|
| 100 ng | 400 | 1.1–2.5 | 0.8–1.5 | 1.2 | Low |
| 10 ng | 40 | 2.1–3.5 | 0.8–3.3 | 1.9 | 0–3 mut/kb |
| 1 ng | 4 | 3.2–4.5 | 3.3–7.2 | 5.3 | Medium |
| 100 pg | 0.4 | 4.2–5.6 | 2.7–11.7 | 5.9 | 3–8 mut/kb |
| 10 pg | 0.04 | 5.2–6.6 | 5.2–11.7 | 6.6 |  |
| Double PCR |  | 5.7–12.8 | 6.7–14.1 | 10.0 | High 6–16 mut/kb |
| Triple PCR |  | 8.8–17.5 | 16.1 | 16.1 |  |

Example 6

Terminal Extendase Activity Assay

The Mutazyme amplified PCR product was examined by a terminal extendaseactivity assay to determine whether the products have blunt ends or sticky ends. Taq DNA polymerase amplified products are known to have 3' overhangs, which are predominantly 3' dAs.

Two primers were used:

```
Primer #1
5'CCA TGA TTA CGC CAA GCG CGC AAT TAA CCC TCA C
(SEQ ID NO:9)

Primer #2
5'GTG AGG GTT AAT TGC GCG CTT GGC GTA ATC ATG G
(SEQ ID NO:10)
```

100 ng of primer #1 was 5' end labeled with $\gamma^{33}$p dATP and the KinAce-It kit (Cat #200390). The products were purified with a NucTrap column (Cat#400701). The final volume was 120 μl at 20,000 cpms/μl. 100 ng of primer #2 was annealed to primer #1 to create a blunt ended double stranded template. A 10 μl extension reaction was prepared consisting of 1× buffer (the pH 8.8 buffer or Taq PCR buffer as used for Taq2000, Cat #400701), 200 μM of one dNTP, 1 μl of oligo template (0.8 ng), and 2.5 units of Mutazyme or Taq2000 DNA polymerase. Extension was carried out for 10 minutes at 72° C. in a Robocycler 40 with a hot top. 3 μl of Novex loading dye was added. Samples were heated to 85° C. and run on a 6% CastAway gel (cat#401094). Autoradiography was performed for 2 days at room temperature.

Figure 2:
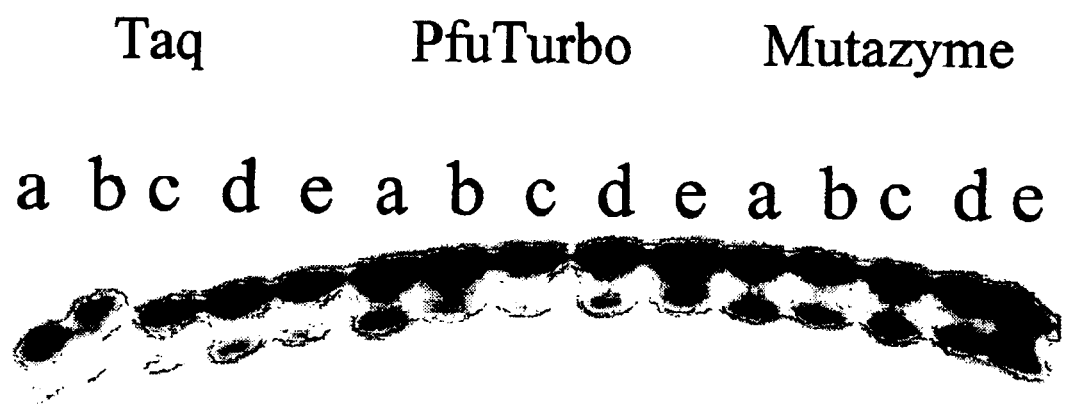
FIG. 2 shows the terminal extendase activity of DNA polymerases. Extension reactions were carried out as described in Example 6 in the presence of: a) 0 μM dNTP, b) 200 μM dATP, c) 200 μM dCTP, d) 200 μM dGTP e) 200 μM dTTP. Autoradiogram is from a 6% CastAway gel.

As shown in FIG. 2, Taq2000 added one A to the end of the fragment, but did not add C, G, or T. Mutazyme did not extend with any of the four dNTPs. Therefore, PCR products produced with Mutazyme have blunt ends.

The foregoing is merely illustrative of the invention and is not intended to limit the invention to the disclosed compositions, kits and methods. Variation and changes are intended to be within the scope and nature of the invention.

Example 7 exo− JDF-3 DNA polymerase for error prone PCR.

exo− JDF-3 was used for error prone PCR in different buffers, with different concentrations of $Mn^{2+}$ and $Mg^{2+}$ (separate and combined), and different concentrations of dNTPs (balanced and different ratios). Highest product yields were obtained using Taq PCR buffer (50 mM KCl, 10 mM Tris HCl (pH 8.8), 0.1% gelatin, 1.5 mM $MgCl_2$). In reactions employing $Mn^{2+}$, it was found that JDF-3 produced amplification product in the presence of 0.5 mM $MnCl_2$, and that product yields were highest when $MgCl_2$ was completely omitted from $Mn^{2+}$-containing reactions.

Because exo−JDF-3 could amplify in the presence of $Mn^{2+}$ alone, unbalanced dNTPs were not used to further increase its error rate. Instead, balanced dNTPs were used. It was found that 0.45–1.0 mM each dNTP gave better yields than 200 uM each dNTP. Thus final error prone PCR conditions with exo− JDF-3 are 5U DNA polymerase, 1× Mg-free Taq PCR buffer, 0.5 mM $MnCl_2$, and 0.45 mM each dNTP.

The following reaction mixture was used with exo⁻ JDF-3 DNA polymerase mutagenesis:

| | |
|---|---|
| 1× | magnesium free *Taq* Buffer (Stratagene catalog #200530) |
| 450 μM | each deoxynucleotide (dGTP, dATP, TTP and dCTP) |
| 2 ng/μl | Primer 923 (also called 490) |
| 2 ng/μl | Primer 721 |
| 0.1 u/μl | exo⁻ JDF-3 DNA polymerase |
| 0.5 mM | $MnCl_2$ |
| 0.1 pM | plasmid DNA |

PCRs were carried out using Stratagene's ROBOCYCLER™ 40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
5) Repeat steps 2 through 4 thirty times.

It is understood that the foregoing detailed description is given merely by way of illustration and that modifications and variations may be made therein without departing from the spirit and scope of the invention.

REFERENCES

1. Andre, P., Kim, A., Khrapko, K. and Thilly, W. G. (1997) Fidelity and mutational spectrum of Pfu DNA polymerase on a human mitochondrial DNA sequence. *Genome Res.* 7:843–852
2. Ausubel et al., John Weley & Sons, Inc., 1997, *Current Protocols in Molecular Biolog*
3. Berger, SL, 1994, Annual Biochem. 222:290–293
4. Borns, M. and Hogrefe, H. (2000) Unique DNA polymerase formulation excels in a broad range of PCR applications. *Strategies* 13(1)
5. Cadwell, R. C. and Joyce, G. F. 1992. Randomization of genes by PCR mutagenesis. PCR Methods Appl. 2:28–33
6. Cariello et al., 1991, *Nucleic Acids Res,* 19:4193
7. Cherry, J. R. Lamsa, M. H., Schneider, P., Vind, J., Svendsen, A., Jones, A., and Pedersen, A. H. 1999. Directed evolution of a fungal peroxidase. Nat. Biotechnol. 17:379–384
8. Chien et al., 1976, J. Bacteoriol, 127:1550
9. Cline et al., 1996, *Nucleic acid Research,* 24:3546–3551
10. Cline, J., Braman, J. C. and Hogrefe, H. H. (1996) PCR fidelity of Pfu DNA polymerase and other thermostable DNA polymerases. *Nucleic Acids Res.* 24(18):3546–3551
11. Daugherty, P. S., Chen, G., Iverson, B. L., and Georgiou, G. 2000. Quantitative analysis of the effect of the mutation frequency on the affinity maturation of single chain Fv antibodies. Proc. Natl. Acad. Sci. U.S.A. 97:2029–2034
12. Diaz and Sabino, 1998 *Braz J. Med. Res,* 31:1239
13. Eckert, K. A. and Kunkel, T. A. (90) Nucl. Acids Res. 18:3739–44
14. Eckert, K. A. and Kunkel, T. A. (91) PCR Methods Appl. 1:17–24
15. Fromant, M, Blanquet, S. and Plateau, P. 1995. Direct random mutagenesis of gene-sized DNA fragments using polymerase chain reaction. Anal Biochem. 224(1) :347–353
16. Hogrefe, H., Scott, B., Nielson, K., Hedden, V., Hansen, C., Cline, J., Bai, F., Amberg, J., Allen, R., Madden, M.(1997) Novel PCR enhancing factor improves performance of Pfu DNA polymerase. *Strategies* 10(3):93–96
17. Hu, G. (1993) DNA polymerase-catalyzed addition of nontemplated extra nucleotides to the 3' end of a DNA fragment. *DNA Cell Biol* 12(8):763–770
18. Juncosa-Ginesta et al., 1994, *Biotechniques,* 16:820
19. Jung, et al, 1987, *Proc. Natl. Acad. Sci. U.S.A.* 84:8287
20. Keohavong, P., Ling, L., Dias, C. and Thilly, W. G. (1993) Predominant mutations induced by the *Thermococcus litoralis,* Vent polymerase during DNA amplification in vitro. PCR Methods Applic. 2:288–292
21. Landre P A, Celfand D H, and Watson E M, in PCR Strategies, Academic Press, 1995, page 3–16
22. Lecomte and Doubleday, 1983, *Nucleic Acids Res.* 11:7505
23. Leung, D. W., Chen, E., and Goeddel, D. V. 1989. A method for random mutagenesis of a defined DNA segment using a modified polymerase chain reaction. Technique 1:11–15
24. Ling, L. L., Keohavong, P, Dias, C., and Thilly, W. G. (91) PCR Methods Appl. 1:63–69
25. Lundberg et al., 1991, *Gene,* 108:1
26. Melnikov, A. and Youngman, P. J. (1999) Random mutagenesis by recombinational capture of PCR products in *Bacillus subtilis* and *Acinetobacter calcoaceticus*. Nucleic Acids Res. 27(4):1056–1062
27. Mullis and Faloona, 1987, *Methods Enzymol.,* 155:335
28. Myers and Gelfand 1991, *Biochemistry* 30:7661
29. Nishiya, Y. and Imanaka, T. 1994. Alteration of substrate specificity and optimum pH of sarcosine oxidase by random and site-directed mutagenesis. Appl. Env. Microbiol. 60:4213–4215
30. Nordstrom et al., 1981, *J. Biol. Chem.* 256:3112
31. Patel, P H., Kawate, H., Adman, E., Ashbach, M., and Loeb, L A. 2001. J. Biol. Chem. 276:5044–5051
32. Sambrook et al., *Molecular Cloning* second edition, Cold Spring Harbor Laboratory Press, Cold Spring Harbor, N.Y. (1989)
33. Shafikhani, R A, Feviari E., and Schellenberger V., 1997, Generation of large libraries of random mutants in *Bacillus subtilis* by PCR-based plasmid multimerization, Biotechniques 23:304–310
34. Shafikhani, S., Siegel, R. A., Ferrari, E. and Schellenberger, V. (1997) Generation of large libraries of random mutants in *Bacillus subtilis* by PCR-based plasmid multimerization. *Biotechniques* 23(2) 304–310
35. Southworth et al., 1996, Proc. Natl. Acad. Sci 93:5281
36. Stemmer, W. P. 1994. DNA shuffling by random fragmentation and reassembly: in vitro recombination for molecular evolution. Proc. Natl. Acad. Sci. USA 91:10747–10751
37. Stenesh and McGowan, 1977, *Biochim Biophys Acta* 475:32
38. Sun y, Hegamyer, G., and Colburn, N H 1993, BioTechniques 15:372–4
39. Takagi et al., 1997, *Appl. Environ. Microbiol.* 63:4504
40. Vartanian, J. P., Henry, M., and Wain-Hobson, S. 1996. Hypermutagenic PCR involving all four transitions and a sizeable proportion of transversions. Nucleic Acids Res. 24:2627–2631
41. Wan, L., Twitchett, M. B., Eltis, L. D., Mauk. A. G., and Smith, M. 1998. In vitro evolution of horse heart myoglobin to increase peroxidase activity. Proc. Natl. Acad. Sci. U.S.A. 95:12825–12831
42. You, L. and Arnold, F. H. 1996. Directed evolution of subtilisin E in *Bacillus subtilis* to enhance total activity in aqueous dimethylformamide. Protein Eng. 9:77–83
43. You, L. and Arnold, F. H. 1996. Directed evolution of subtilisin E in *Bacillus subtilis* to enhance total activity in aqueous dimethylformamide. Protein Eng. 9:77–83

What is claimed is:

1. A composition for PCR mutagenesis comprising an archaeal exo– DNA polymerase which substantially lacks 3' to 5' exonuclease activity, and a protein PCR enhancing factor.

2. The composition of claim 1, wherein said archaeal exo– DNA polymerase is selected from the group consisting of: exo–Tli DNA polymerase, exo– Pfu DNA polymerase, exo–KOD DNA polymerase, exo– JDF-3 DNA polymerase, and exo–PGB-D DNA polymerase.

3. The composition of claim 1, further comprising one or more DNA polymerases selected from the group consisting of Taq DNA polymerase, Tth DNA polymerase, UlTma DNA polymerase, exo–Tli DNA polymerase, exo– Pfu DNA polymerase, exo– Tma DNA polymerase, exo– KOD DNA polymerase, exo– JDF-3 DNA polymerase, and exo–PGB-D DNA polymerase, wherein said one or more DNA polymerases are different from said archaeal DNA polymerase.

4. The composition of claim 1, 2, or 3, further comprising a PCR buffer useful for generating a mutated amplified product at a given mutation frequency.

5. The composition of claim 4, wherein said PCR buffer lacks $Mn^{2+}$.

6. The composition of claim 1, 2, or 3, further comprising equivalent molar amounts of dATP, dTTP, dGTP, and dCTP.

7. A kit for PCR mutagenesis comprising an archaeal exo– DNA polymerase, a protein PCR enhancing factor, and packaging means therefor.

8. The kit of claim 7, wherein said archaeal exo– DNA polymerase is selected from the group consisting of: exo–Tli DNA polymerase, exo– Pfu DNA polymerase, exo– Tma DNA polymerase, exo– KOD DNA polymerase, exo– JDF-3 DNA polymerase, and exo– PGB-D DNA polymerase.

9. The kit of claim 7, further comprising one or more polymerases selected from a group consisting of Taq DNA polymerase, Tth DNA polymerase, UlTma DNA polymerase, exo–Tli DNA polymerase, exo– Pfu DNA polymerase, exo–Tli DNA polymerase, exo– Tma DNA polymerase, exo– KOD DNA polymerase, exo– JDF-3 DNA polymerase, and exo–PGB-D DNA polymerase, wherein said one or more DNA polymerases are different from said archaeal DNA polymerase.

10. The kit of claim 7, 8, or 9, further comprising a PCR buffer useful for generating a mutated amplified product at a given mutation frequency.

11. The kit of claim 10, wherein said PCR buffer lacks $Mn^{2+}$.

12. The kit of claim 7, 8, or 9, further comprising equivalent molar amounts of dATP, dTTP, dGTP, and dCTP.

13. A method of PCR amplification for mutagenesis comprising incubating a reaction mixture comprising a nucleic acid template, at least two PCR primers, an archaeal exo– DNA polymerase which sunstantially lacks 3' to 5' exonuclease activity, and a protein PCR enhancing factor under conditions which permit amplification of said nucleic acid template by said archaeal exo– DNA polymerase to produce a mutated amplified product.

14. The method of claim 13, wherein said archaeal exo– DNA polymerase is selected from the group consisting of: Taq DNA polymerase, Tth DNA polymerase, UlTma DNA polymerase, exo–Tli DNA polymerase, exo– Pfu DNA polymerase, exo– Tma DNA polymerase, exo– KOD DNA polymerase, exo– JDF-3 DNA polymerase, and exo–PGB-D DNA polymerase.

15. The method of claim 13, wherein said incubating step further comprises incubating one or more exo– DNA polymerases selected from a group consisting of: Taq DNA polymerase, Tth DNA polymerase, UlTma DNA polymerase, exo–Tli DNA polymerase, exo– Pfu DNA polymerase, exo–Tli DNA polymerase, exo– Tma DNA polymerase, exo– KOD DNA polymerase, exo– JDF-3 DNA polymerase, and exo–PGB-D DNA polymerase in said reaction mixture, wherein said one or more DNA polymerases are different from said archaeal DNA polymerase.

16. The method of claim 13, 14, or 15, wherein said incubating step is performed in a PCR reaction buffer lacking $Mn^{2+}$.

17. The method of claim 13, 14, or 15, wherein said incubating step further comprises incubating equivalent molar amounts of dATP, dTTP, dGTP, and dCTP.

18. The method of claim 13, wherein said incubating step generates said mutated amplified product at a given mutation frequency using a given amount of said nucleic acid template.

19. The method of claim 18, wherein a first said incubating step generates a first said mutated amplified product at a first given frequency using a first selected amount of said nucleic acid template, and a second said incubating step generates a second said mutated amplified product at a second given frequency using a second selected amount of said nucleic acid template, wherein said first incubating step and second incubating step comprise a single buffer composition.

20. The method of claim 19, further comprising subsequently repeating one or more additional incubating step using a portion of or the total amplified product of a preceding incubating step as template.

21. The method of claim 18, wherein said mutation frequency is proportional to the amount of said nucleic acid template.

22. The method of claim 13, 14, or 15, wherein said incubating step comprises 1 pg to 1 μg of said nucleic acid template.

23. The method of claim 18, wherein said incubating produces said mutated amplified product from said nucleic acid template at a mutation frequency of 1,000 to 16,000 mutations or more per $10^6$ base pairs.

24. The method of claim 22, wherein said incubating step comprises 10–100 ng of said nucleic acid template.

25. The method of claim 24, wherein said incubating step produces said mutated amplified product at a mutation frequency of 1,000 to 3,000 mutations per $10^6$ base pair.

26. The method of claim 22, wherein said incubating step comprises 10 pg to 10 ng of said nucleic acid template.

27. The method of claim 26, wherein said incubating step produces said mutated amplified product at a mutation frequency of 3,000 to 7,000 mutations per $10^6$ base pairs.

28. The method of claim 26, wherein said incubating steps produces said mutated amplified product at a mutation frequency of 7,000 to 16,000 or more mutations per $10^6$ base pairs.

29. The method of claim 28, further comprising subsequently repeating one or more times an additional incubating step using a portion of or the total amplified product of a preceding incubating as template.

30. The method of claim 13, 14, or 15, wherein said incubating step comprises a nucleic acid template of 0.1 kb to 10 kb in length.

31. The method of claim 13, 14, or 15, wherein said incubating step produces amplified product at a yield of 0.5–10 μg.

* * * * *

SEQUENCE LISTING

<160> NUMBER OF SEQ ID NOS: 10

<210> SEQ ID NO 1
<211> LENGTH: 620
<212> TYPE: DNA
<213> ORGANISM: Escherichia coli

<400> SEQUENCE: 1

```
ctcgaggaac aagacccgtt actagtactt atccctgatt ctgtggataa ccgtattacc      60
gcctttgagt gagctgatac cgctcgccgc agccgaacga ccgagcgcag cgagtcagtg     120
agcgaggaag cggaagagcg cccaatacgc aaaccgcctc tccccgcgcg ttggccgatt     180
cattaatgca gctggcacga caggtttccc gactggaaag cgggcagtga gcgcaacgca     240
attaatgtga gttagctcac tcattaggca ccccaggctt tacactttat gcttccggct     300
cgtatgttgt gtggaattgt gagcggataa caatttcaca caggaaacag ctatgaccat     360
gatacgccaa gcgcgctcac tggccgtcgt tttacaacgt cgtgactggg aaaaccctgg     420
cgttacccaa cttaatcgcc ttgcagcaca tcccccttc gccagctggc gtaatagcga     480
agaggcccgc accgatcgcc cttcccaaca gttgcgcagc ctgaatggcg aatgggacgc     540
gccctgtagc ggcgcattaa gcgcggcggg tgtggtggtt acgcgcagcg tgtcgacgtt     600
aacttgtcgt cgtcgaattc                                                 620
```

<210> SEQ ID NO 2
<211> LENGTH: 24
<212> TYPE: DNA
<213> ORGANISM: artificial sequence
<220> FEATURE:
<223> OTHER INFORMATION: primer

<400> SEQUENCE: 2

```
ggaacaagac ccgttactag tact                                          24
```

<210> SEQ ID NO 3
<211> LENGTH: 24
<212> TYPE: DNA
<213> ORGANISM: artificial sequence
<220> FEATURE:
<223> OTHER INFORMATION: primer

<400> SEQUENCE: 3

```
gacgacgaca agttaacgtc gaca                                          24
```

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4

```
gctagttatt gctcagcggt g                                             21
```

<210> SEQ ID NO 5
<211> LENGTH: 33
<212> TYPE: DNA
<213> ORGANISM: artificial sequence
<220> FEATURE:
<223> OTHER INFORMATION: primer

<400> SEQUENCE: 5

```
gacgacgaca agatgaccct aaatatagaa gat                                33
```

<210> SEQ ID NO 6
<211> LENGTH: 35
<212> TYPE: DNA
<213> ORGANISM: artificial sequence
<220> FEATURE:
<223> OTHER INFORMATION: primer

<400> SEQUENCE: 6

```
ggaacaagac ccgtcaagct ttgcaggtct cagtg                              35
```

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7

```
ggctgccgac cccgggggtg g                                             21
```

<210> SEQ ID NO 8
<211> LENGTH: 21
<212> TYPE: DNA
<213> ORGANISM: artificial sequence
<220> FEATURE:
<223> OTHER INFORMATION: primer

<400> SEQUENCE: 8

```
cgaaccccag agtcccgctc a                                             21
```

<210> SEQ ID NO 9
<211> LENGTH: 34
<212> TYPE: DNA
<213> ORGANISM: artificial sequence

```
-continued

<220> FEATURE:
<223> OTHER INFORMATION: primer

<400> SEQUENCE: 9
ccatgattac gccaagcgcg caattaaccc tcac                                34

<210> SEQ ID NO 10
<211> LENGTH: 34
<212> TYPE: DNA
<213> ORGANISM: artificial sequence
<220> FEATURE:
<223> OTHER INFORMATION: primer

<400> SEQUENCE: 10
gtgagggtta attgcgcgct tggcgtaatc atgg                                34
```